(12) United States Patent
Heber et al.

(10) Patent No.: US 9,433,805 B2
(45) Date of Patent: Sep. 6, 2016

(54) METHOD FOR DERMAL REGENERATION BY ADMINISTERING AN ETHER CROSS-LINKED GLUCOMANNAN/HYALURONIC ACID COMPOSITION

(75) Inventors: Geoffrey Heber, Broadway (AU); Nicholas Patrick John Stamford, Gladesville (AU)

(73) Assignee: ULTRACEUTICALS R&D PTY LTD. (AU)

(*) Notice: Subject to any disclaimer, the term of this patent is extended or adjusted under 35 U.S.C. 154(b) by 558 days.

(21) Appl. No.: 12/681,391

(22) PCT Filed: Oct. 3, 2008

(86) PCT No.: PCT/AU2008/001474
§ 371 (c)(1),
(2), (4) Date: Jun. 23, 2010

(87) PCT Pub. No.: WO2009/043111
PCT Pub. Date: Apr. 9, 2009

(65) Prior Publication Data
US 2010/0255076 A1    Oct. 7, 2010

(30) Foreign Application Priority Data
Oct. 4, 2007    (AU) ................... 2007905441

(51) Int. Cl.
*A61Q 19/08* (2006.01)
*A61K 8/73* (2006.01)
*A61K 31/736* (2006.01)
*A61K 8/02* (2006.01)
*A61K 8/04* (2006.01)

(52) U.S. Cl.
CPC .......... *A61Q 19/08* (2013.01); *A61K 8/0241* (2013.01); *A61K 8/042* (2013.01); *A61K 8/73* (2013.01); *A61K 8/735* (2013.01); *A61K 8/736* (2013.01); *A61K 31/736* (2013.01); *A61K 2800/412* (2013.01); *A61K 2800/56* (2013.01); *A61K 2800/91* (2013.01)

(58) Field of Classification Search
CPC .... A61K 9/127; A61K 31/715; A61P 17/00; C08B 37/0072; C08B 37/0087; C08J 3/246; C08J 2405/08; C08J 2305/08
See application file for complete search history.

(56) References Cited

U.S. PATENT DOCUMENTS

| | | | |
|---|---|---|---|
| 4,716,224 A | 12/1987 | Sakurai et al. | |
| 4,784,986 A | 11/1988 | Usher | |
| 4,851,224 A * | 7/1989 | McAnalley | A61K 8/97 424/744 |
| 5,703,060 A * | 12/1997 | McAnalley | A23L 2/52 514/54 |
| 5,728,391 A | 3/1998 | Ikeya et al. | |
| 6,544,503 B1 * | 4/2003 | Vanderhoff | A61L 27/16 424/422 |
| 2004/0171580 A1 * | 9/2004 | Stucchi et al. | 514/54 |

FOREIGN PATENT DOCUMENTS

| | | | |
|---|---|---|---|
| FR | 2773324 | * | 7/1999 |
| JP | 57095905 | | 6/1982 |
| JP | 2005-112762 | | 4/2005 |
| WO | 86/00079 A1 | | 1/1986 |
| WO | WO 01/02479 | | 1/2001 |
| WO | WO 2004092223 | * | 10/2004 ............ C08B 37/08 |

OTHER PUBLICATIONS

Amsellem., machine translation of FR 2773324, retrieved from the internet <http://worldwide.espacenet.com/?locale=en_EP> on Jun. 25, 2012, 3 pages.*
Daughton, C. G. (2003). Cradle-to-cradle stewardship of drugs for minimizing their environmental disposition while promoting human health. I. Rationale for and avenues toward a green pharmacy. Environmental Health Perspectives, 111(5), 757.*
PCT International Preliminary Report on Patentability for PCT International Application No. PCT/AU2008/001474, dated Nov. 6, 2009.
Boulle, K., R., G., Kono, T., Nathan, M., Tezel, A., Roca-Martinez, J.-X., et al. (2013). A Review of the Metabolism of 1,4-Butanediol Diglycidyl Ether—Crosslinked Hyaluronic Acid Dermal Fillers. Dermatologic Surgery, 39 (12), 1758-1766.
Dumitriu, S. (1998). Polysaccharides: Structural Diversity and Functional Versatility. Marcel Dekker.
Kenne, L., Gohil, S., Nilsson, E. M., Karlsson, A., Ericsson, D., Kenne, A. H., et al. (2013). Modification and cross-linking parameters in hyaluronic acid hydrogels—Definitions and analytical methods. Carbohydrate Polymers, 91, 410-418.
Montagna, W. (1955). Histology and Chemistry of Human Skin. J. Biophysic. and Biochem. Cytol., 1 (1), 13-16.
Nair, L. S., & Laurencin, C. T. (2007). Biodegradable polymers as biomaterials. Prog. Polym. Sci., 32, 762-798.
Park, H., Park, K., & Shalaby, W. S. (2011). Biodegradable Hydrogels for Drug Delivery. CRC Press.

(Continued)

Primary Examiner — Eric Olson
Assistant Examiner — Dale R Miller
(74) Attorney, Agent, or Firm — J.A. Lindeman & Co., PLLC

(57) ABSTRACT

The present invention relates to glucommannan oligosaccharides and polysaccharides that possess one or more properties selected from skin regeneration, wound healing and skin augmentation. More particularly, the invention relates to the use of glucomannan oligosaccharides and polysaccharides for one or more of skin regeneration, wound healing and skin augmentation agents in a mammal. The invention also relates to a pharmaceutical formulation for treating skin of a subject comprising an active component comprising glucomannan in a suitable diluent, excipient or physical form such as dermal scaffold or sponge, the active component being capable of promoting an accumulation of fibroblasts in the skin and stimulating production of collagen in the skin.

18 Claims, 15 Drawing Sheets

(56) References Cited

OTHER PUBLICATIONS

Qiu, Y., Chen, Y., Zhang, G. G., Liu, L., & Porter, W. (2009). Developing Solid Oral Dosage Forms: Pharmaceutical Theory & Practice. Academic Press.

Ratner, B., Hoffman, A., Schoen, F., & Lemons, J. (2004). Biomaterials Science: An Introduction to Materials in Medicine, 2nd Edition. Elsevier.

Strom, A., Larsson, A., & Okay, O. (2015). Preparation and physical properties of hyaluronic acid-based cryogels. J. Appl. Polym. Sci., 132 (29), 42194-42205.

Testa, B., & Mayer, J. M. (2003). Hydrolysis in Drug and Prodrug Metabolism. Wiley.

Wicks, Z. W., Jones, F. N., Pappas, S. P., & Wicks, D. A. (2007). Organic Coatings: Science and Technology. Wiley.

Hamman "Composition and applications of Aloe vera leaf gel," Molecules 13.8 (2008): 1599-1616.

Li, et al. "Review of konjac glucomannan: isolation, structure, chain conformation and bioactivities," Organization (WHO) 4 (2013): 8.

Talmadge et al, "Fractionation of Aloe vera L. inner gel, purification and molecular profiling of activity," International Immunopharmacology 4.14 (2004): 1757-1773.

* cited by examiner

A

B

A

B

A

B

A

B

A

B

A

B

A

B

A

B

A

B

A

B

A

B

METHOD FOR DERMAL REGENERATION BY ADMINISTERING AN ETHER CROSS-LINKED GLUCOMANNAN/HYALURONIC ACID COMPOSITION

TECHNICAL FIELD

The present invention relates to glucommannan oligosaccharides and polysaccharides that possess one or more properties selected from skin regeneration, wound healing and skin augmentation. More particularly, the invention relates to the use of glucomannan oligosaccharides and polysaccharides for one or more of skin regeneration, wound healing and skin augmentation agents in a mammal.

BACKGROUND ART

The cutaneous tissue contains cellular protein and glycoprotein components which together influence the thickness and form of the tissue. Fibroblasts are a common cellular constituent of the skin and produce various proteins that are important structural components of cutaneous tissue. One such protein is collagen which can be and is widely used to artificially augment cutaneous shape. A characteristic of ageing and wrinkled skin is a reduction in cellularity. A potential goal of treating ageing or wrinkled skin could be to increase the cellularity in an affected area of skin. A further desirable effect of an increase in cellularity may be increased production of extracellular dermal components, including for example, collagen.

One of the clinical features of treating damaged skin with retinoic acid, believed to be of cosmetic benefit, is an increase in new collagen synthesis. Another commonly used treatment for skin wrinkling, glycolic acid, has been shown to increase collagen synthesis in fibroblast cultures in vitro and it has been suggested that this effect may occur in vivo and account for the apparent beneficial effects associated with glycolic acid use. It has also been proposed that a deficiency of superficial dermal collagen is the main cause of photo-ageing.

U.S. Pat. No. 5,980,916 describes the use of laminarin or laminarin-derived oligosaccharides as a "cosmetic or pharmaceutical, particularly dermatological". Laminarin is a polysaccharide derived from *Laminaria* spp seaweed and is a linear polymer composed of beta-1,3-D-glucose and a small amount of beta-1,6-D-glucose linkages. This patent describes laminarin, oligosaccharides derived therefrom, and compositions containing these substances as having stimulating, regenerating, conditioning and energising effects on human dermis fibroblasts and human epidermis keratinocytes. It does not teach or suggest the use of any oligosaccharides or polysaccharides other than those from laminarin as a means for stimulating skin cells (eg, fibroblasts and keratinocytes).

U.S. Pat. No. 5,916,880 describes the use of a sulphate saccharide or a salt or complex thereof for the preparation of a medicament for topical application to the skin. This patent also describes a method for cosmetically treating skin to reduce wrinkles, the method comprising topically applying to affected areas of skin a cosmetically effective amount of at least one compound selected from the group consisting of sulfate monosaccharides, sulfate disaccharides, and salts and complexes thereof. U.S. Pat. No. 5,916,880 does not disclose the use of any agents other than sulfate sugars for the treatment of skin wrinkles. U.S. Pat. No. 5,916,880 states that the saccharide is preferably a polysulphated or persulphated saccharide, which means that two or more, possibly all, sulphur-containing moieties are present as substituents on the carbohydrate moiety. The compounds and methods disclosed in this patent do not teach or imply that non-sulfated oligosaccharides or polysaccharides could have a skin augmenting or tissue regeneration activity.

WO 03/068243 and corresponding Australian patent No. 2003245471 describe oligosaccharides and polysaccharides based either on glucose or mannose, but not both, which have skin augmenting activity. Glucose based oligosaccharides or polysaccharides described are amylopectin, amylose, 1,4-D-glucose oligosaccharides isolated by acid hydrolysis of amylose, maltopentaose, maltohexaose, maltoheptaose, alpha-1',4-maltooctaose, maltononaose, maltodecanose, maltoundecanose and maltododecanose. Mannose based oligosaccharides or polysaccharides described include 1,4-beta-D-mannose oligosaccharides and polysaccharides, the latter being commonly referred to as 1,4-beta-D-mannans. Other materials described include the 1,4-beta-D-mannose polymer isolated from the seeds of Phoenix canariensis and the oligosaccharides isolated therefrom. 1,4-Beta-D-mannose oligosaccharides of from 4 to 12 mannose units are described, as is mannan from Saccharomyces cerevisiae; exocellular phosphomannan produced by *Pichia holstii*, purified D-mannose high molecular weight acid-resistant polysaccharide core of the exocellular phosphomannan produced by *Pichia holstii*; 6-O-phospho-alpha-D-mannose-(1,3)-alpha-D-mannose-(1,3)-alpha-D-mannose-(1,3)-alpha-D-mannose-(1,2)-alpha-D-mannose, beta-1,4-mannopentaose, beta-1,4-mannohexaose; beta-1,4-mannoheptaose, beta-1,4-mannooctaose, beta-1,4-mannononaose, beta-1,4-mannodecanose, beta-1,4-mannoundecanose and beta-1,4-mannododecanose.

WO 03/068243 does not describe glucomannan oligosaccharides or polysaccharides, or any oligosaccharides or polysaccharides based on both glucose and mannan, as is glucomannan. The compounds and methods disclosed in WO 03/068243 also do not teach or suggest that oligosaccharides or polysaccharides based on both glucose and mannan, such as glucomannan, could have skin regeneration, wound healing or skin augmenting properties.

Glucomannan is most commonly derived from konjac root (*Amorphophallus konjac*). *Amorphophallus konjac* is a perennial herbaceous herb. It grows in mountain or hilly areas in subtropical regions mainly in the South East of Asia. It has been used as a food and food additive in China and Japan for more than 1000 years. The fresh konjac tuber contains an average of 13% dry matter. Sixty four percent of the dry matter is glucomannan and 30% is starch. The molecular mass of glucomannan derived from the konjac tuber is 200,000 to 2,000,000 Da, depending upon konjac species or variety and processing method. Glucomannan can absorb up to 200 times its weight in water. Glucomannan from the konjac tuber is relatively inexpensive and readily available, particularly in comparison with the agents listed in WO 03/068243.

Glucomannan derived from the konjac root is a high molecular weight polysaccharide formed from residues of glucose (G) and mannose (M) in a proportion of 5:8 bound together by β-1,4-linkages. The basic polymeric repeating unit has the pattern: GGMMGMMMMGGM. Glucomannan is not a linear molecule and has short side chains of 11-16 monosaccharides occurring at intervals of 50-60 units of the main chain attached by 1β→3 linkages. Acetyl groups on carbon 6 are located on every 9-19th sugar unit of the main chain. These acetyl groups contribute to the solubility and gelling properties. If the acetyl groups are removed under mild alkaline conditions, the molecule will produce heat stable gels. Glucomannans from other sources may contain glucose and mannose in different proportions and/or different sequences, as well as minor amounts of sugars other than glucose and mannose. All such forms of glucomannan are encompassed by the present invention.

Konjac glucomannan as a food additive is approved in Canada by Health Canada, is FDA approved as GRAS in the United States and is approved by the EU under E425, Annex V, food additives, 1998, EU.

The present inventor has found that glucomannan (oligosaccharides and polysaccharides) has skin regeneration, wound healing and skin augmenting activity.

DISCLOSURE OF INVENTION

The present invention generally relates to the use of the polysaccharide glucomannan or oligosaccharides derived from glucomannan (also referred to herein as 'glucomannan oligosaccharides'), which, when applied to or into an area of skin or subcutaneous tissue, can attract fibroblasts and stimulate production of collagen to provide augmentation, regeneration or healing of the treated skin.

In a first aspect, the present invention provides a method for treating a condition of skin of a subject, the method comprising delivering to the skin an active component comprising a glucomannan polysaccharide, an oligosaccharide derived from glucomannan, mixtures or combinations thereof, physically modified analogues thereof and chemically modified analogues thereof, wherein after delivery, the active component promotes an accumulation of fibroblasts in the skin at or near to the site of delivery and stimulates, ie, increases, production of collagen in the skin.

In a second aspect, the present invention provides the use of an active component comprising a glucomannan polysaccharide, an oligosaccharide derived from glucomannan, mixtures or combinations thereof, physically modified analogues thereof and chemically modified analogues thereof for the manufacture of a medicament for treating skin of a subject, wherein the active component promotes an accumulation of fibroblasts in the skin at or near to the site of delivery and stimulates, ie, increases, production of collagen.

The treating of the skin may be to regenerate, heal, augment, alleviate scarring or signs of ageing, heal wounds or ulcers, regenerate atrophic skin due to trauma, disease or ageing, smooth wrinkles, increase firmness and elasticity in ageing skin, or any combination thereof.

In a preferred embodiment the active component is a glucomannan oligosaccharide. In another preferred embodiment the active component is a glucommanan polysaccharide.

Preferably, the glucomannan oligosaccharide or polysaccharide is derived from konjac root (Amorphophallus konjac). However, glucomannan is widespread as a cell wall component in a variety of plants, yeasts, algae, and mushrooms. Other plant sources include but are not limited to Parana pine (Araucaria angustifolia), Scots pine (Pinus sylvestris), Jack pine (Pinus Banksiana), Eastern white pine (Pinus strobus), Radiata pine (Pinus radiata), Norwegian spruce (Picea abies), White spruce (Picea glauca), European ash (Fraxinus excelsior), Sugar maple (Acer saccharum), Hornbeam (Carpinus betulus), Tamarack (Larix larcinia), Bluebell (Scylla nonscriopta), Polygonatum species, Poet's Daffodil (Narcissus poeticus), the tuberous roots of Eremurus tadshicorum, Eremurus zangezuricus, Eremurua altaicus, Eremurus cristatus, Bletilla striata, Arum korolkovii and Orchis morio, the leaves of Aloe barbadensis, Aloe Vahombe, the bulbs of ester lily and Lilium testaceum and the seeds of Libyan dates, Iris sogdiana and San-plain lupin (Lupinus varius). Glucomannan has also been shown to be synthesised by Mung bean seedlings and pea seedlings (Pisum sativum). Yeast sources of glucomannan include but are not limited to the cell walls of Rhodotorula glutinis, Sporobolomyces salmonicolor, Wheat stem rust (Puccinia graminis iritici), Cryptococcus laurentii, Saccharomyces cerevisiae, Candida utilis and Candida albicans. An alga source includes but is not limited to the red alga Kappaphycus alvarezii. A mushroom source includes but is not limited to Agaricus blazei. Glucomannan can be synthesized enzymatically in vitro. This list is not exclusive and it is appreciated that new sources of glucomannan may be found in the future.

The present invention also includes the use of chemically modified analogues of the glucomannan oligosaccharides or polysaccharides. Such modification may enhance transdermal penetration or solubility. For example, a lipid moiety, such as palmitic acid, or a carboxymethyl group attached to the oligosaccharide or polysaccharide, might enhance transdermal penetration. Polar lipids inclined to form ionic bonds with glucomannan may be used to enhance percutaneous absorption.

In a preferred embodiment the glucomannan is administered alone. In another preferred embodiment the glucomannan is administered together with another agent. The glucomannan and other agent may be administered separately, simultaneously or sequentially in any order. In another embodiment, the glucomannan and other agent may be present in the same pharmaceutical formulation. The other agent may be collagen, a carbohydrate, or a mixture of carbohydrates. In a preferred embodiment the other agent is collagen. In a preferred embodiment the other agent is a carbohydrate. In another preferred embodiment the other agent is a mixture of carbohydrates. The carbohydrate may be cross-linked. In a preferred embodiment, the carbohydrate may be cross-linked with the glucomannan. In a particularly preferred embodiment the carbohydrate is hyaluronic acid. Examples of pharmaceutically acceptable hyaluronic acid formulations include Restylane™ and Perlane™. The hyaluronic acid may be cross-linked. Examples of cross-linked hyaluronic acid include those described in WO 2004/092223. The glucomannan may be cross-linked with the hyaluronic acid. Suitable cross-linking agents are known in the art and include, but are not limited to butanediol diglycidyl ether.

The subject may be a mammal, eg, a human or an animal. Preferably, the subject is a human. The subject may require skin treatment to aid wound healing, skin regeneration or skin augmentation, eg, to alleviate signs of scarring or ageing.

The active component may be applied parenterally, eg, by injection directly into the skin or subcutaneous tissue, or applied topically to the skin.

The active component may be delivered to the skin at a concentration of about 0.001% to about 100% by weight. Preferably, the oligosaccharide or polysaccharide is delivered to the skin at a concentration of about 0.01% to about 70% by weight. More preferably, the active component is delivered to the skin at a concentration of about 0.1% to about 30% by weight. Even more preferably, the oligosaccharide or polysaccharide is delivered to the skin at a concentration of about 1% to about 20% by weight.

In a third aspect, the present invention provides the use of an active component comprising a glucomannan polysaccharide, an oligosaccharide derived from glucomannan, mixtures or combinations thereof, physically modified analogues thereof and chemically modified analogues thereof for treating skin of a subject, wherein after delivery of the active component to the skin, fibroblasts accumulate in the skin at or near to the site of delivery and collagen is produced in the skin.

In a fourth aspect, the present invention provides a pharmaceutical formulation for treating skin comprising an effective amount of an active component comprising glucomannan polysaccharide, an oligosaccharide derived from glucomannan, mixtures or combinations thereof, physically modified analogues thereof and chemically modified analogues thereof together with a pharmaceutically acceptable diluent, excipient or carrier, or in a physical form such as dermal scaffold or sponge, the active component being capable of promoting an accumulation of fibroblasts in the skin and stimulating, ie, increasing, production of collagen in the skin.

In a preferred embodiment the pharmaceutical formulation is a topical formulation. In another preferred embodiment the pharmaceutical formulation is a parenteral formulation. In a further preferred embodiment the pharmaceutical formulation is in the form of a dermal scaffold or sponge.

For the avoidance of doubt, it is to be understood that in the context of the present invention any one or more aspects or embodiments described herein may be taken in combination with any other one more aspects or embodiments. The present disclosure includes all such combinations.

Throughout this specification, glucomannan polysaccharides, oligosaccharides derived from glucomannan, mixtures or combinations thereof, physically modified analogues thereof and chemically modified analogues thereof may be collectively referred to as "glucomannan".

In the context of the present invention "skin" means the outer covering of living tissue of an animal. It is the largest component of the integumentary system and is made up of multiple layers of epithelial tissues.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred forms will be described with reference to the following drawings and examples.

MODE(S) FOR CARRYING OUT THE INVENTION

Figure 1:
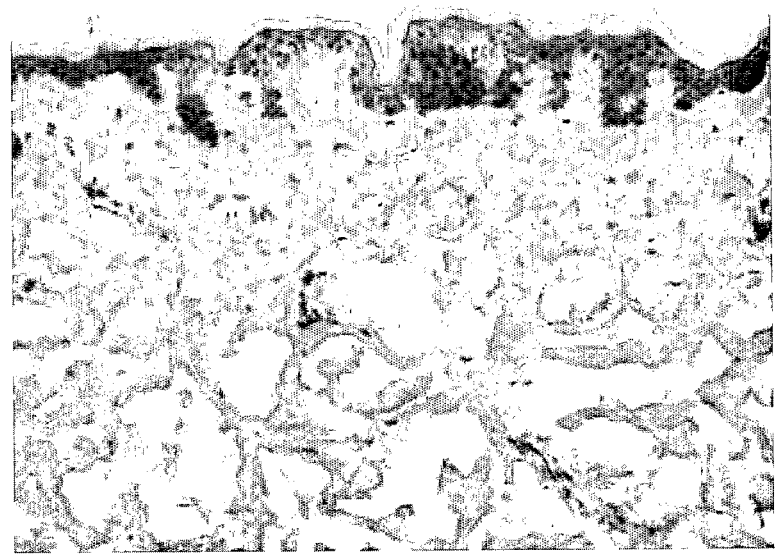
FIG. 1 shows histological sections of human skin tissue from Example 2, anti-human collagen type I antibody (Chemical Credential, ICN) stain (A), showing an increase in collagen I 48 hours following intradermal injection of glucomannan (B).
Figure 1:
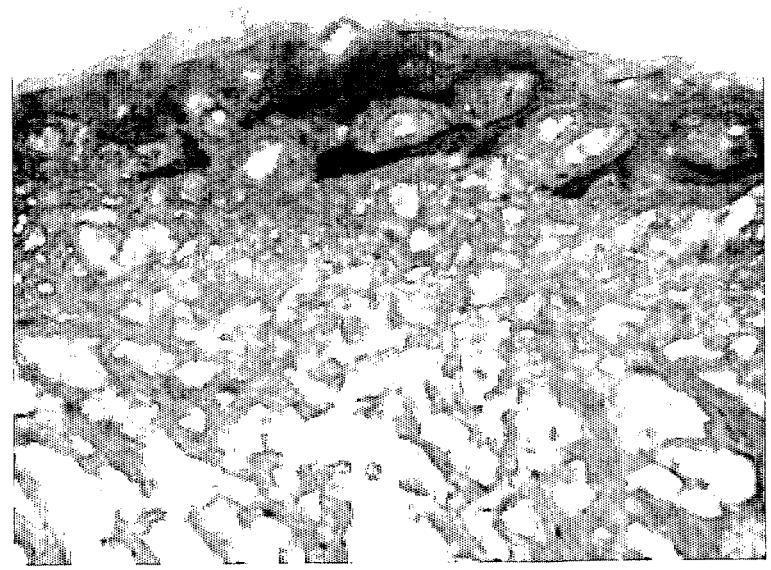

It has now been discovered and is the subject of the present invention that an increase in cellularity in cutaneous tissue, that is the state of the tissue as regards the number of its constituent cells, may be effected by applying glucomannan or derivatives thereof to skin tissue. The increase in cellularity appears to be brought about through migration of cells into the area exposed to the glucomannan. It has also been found that the arrival of these new cells is correlated with an increase in collagen deposition within the area treated. It has been discovered that not all carbohydrates have this cell attracting activity. For example, the efficacy of 1,6-alpha-D-glucose dextran oligosaccharides and dextran polysaccharides (dextrans), is low in attracting fibroblasts and increasing collagen deposition. The cell-attracting property therefore appears to be structure dependent, rather than a property of the entire class of carbohydrates.

It has further been discovered that the newly arrived cells in the treated dermis are largely fibroblastic cells.

The present invention relates to the use of glucomannan oligosaccharides and polysaccharides as skin regeneration and wound healing agents or skin regeneration and augmentation agents. Accordingly, one aspect of the present invention relates to a method of skin regeneration and wound healing of an animal or human subject which comprises administering to the subject an effective amount of glucomannan oligosaccharide or polysaccharide or derivative or analogue thereof.

In another aspect, the invention relates to a method of skin regeneration and augmentation of an animal or human subject which comprises administering to the subject an effective amount of glucomannan oligosaccharide or polysaccharide or derivative or analogue thereof.

In a further aspect the invention relates to the use of glucomannan oligosaccharide or polysaccharide or derivative or analogue thereof in the manufacture of a medicament for skin regeneration and wound healing of an animal or human.

In another aspect the invention relates to the use of glucomannan oligosaccharide or polysaccharide or derivative or analogue thereof in the manufacture of a medicament for skin regeneration and augmentation of an animal or human.

Whilst it is not intended that the present invention should be restricted in any way by a theoretical explanation of the mode of action of the glucomannan in accordance with the invention, it is presently believed that this active compound may exert its tissue augmentation and regeneration effect by attracting fibroblasts to or near the site of administration and inducing collagen deposition at or near this site. Accordingly, the active glucomannan oligosaccharides and polysaccharides or derivatives thereof may include any such compounds containing both glucose and mannose that are effective at promoting fibroblast migration and increasing collagen production at or near the site of their administration.

Without intending to be limited to a particular theory, it is believed by the present inventor that the action of glucomannan may be due to specific interactions with cells rather than a non-specific action. An example of a non-specific action which may result in increased collagen production is inflammation. However, in the present invention increased numbers of inflammatory polymorphonucleocyte cells are not observed following glucomannan treatment. Also, injection of the saccharides glucomannan, yeast mannan and starch into fresh ex vivo human skin resulted in significant increased new collagen being observed in the skin injected with glucomannan, but not in the skin injected with the other saccharides. Injection of mannan into fresh human ex vivo skin did not result in increased numbers of fibroblasts.

The active skin regeneration, wound healing and skin augmentation agents in accordance with the present invention may be used to remodel and treat skin or soft tissue defects including wounds, scars, tissue atrophy or shallow or deep wrinkles of skin, including neck or facial wrinkles.

In accordance with the present invention the glucomannan active agents may be used alone, in combination with one another, in combination with one or more other carbohydrates, eg hyaluronic acid, chitosan, or in combination with other known tissue remodelling agents, eg collagen. In a preferred embodiment glucomannan is not used in combination with another carbohydrate or tissue remodelling agent.

In another preferred embodiment the glucomannan active agent is used in combination with collagen. In one embodiment the ratio of glucomannan to collagen is about 90:10 by weight. In another embodiment the ratio of glucomannan to collagen is about 75:25 75:25 by weight. In a further embodiment the ratio of glucomannan to collagen is about 50:50 50:50 by weight. In a further embodiment the ratio of glucomannan to collagen is about 30:70 by weight. In another embodiment the ratio of glucomannan to collagen is about 25:75 by weight. In a further embodiment the ratio of glucomannan to collagen is about 20:80 by weight. In another embodiment the ratio of glucomannan to collagen is about 15:85 by weight. In a further embodiment the ratio of glucomannan to collagen is about 10:90 by weight. In another embodiment the ratio of glucomannan to collagen is about 5:95 by weight. In a further embodiment the ratio of glucomannan to collagen is about 1:99 by weight.

In another preferred embodiment the glucomannan active agent is used in combination with another carbohydrate. In a preferred embodiment the carbohydrate is hyaluronic acid. In one embodiment the ratio of glucomannan to carbohydrate is about 90:10 by weight. In another embodiment the ratio of glucomannan to carbohydrate is about 75:25 by weight. In a further embodiment the ratio of glucomannan to carbohydrate is about 50:50 by weight. In a further embodiment the ratio of glucomannan to carbohydrate is about 30:70 by weight. In another embodiment the ratio of glucomannan to carbohydrate is about 25:75 by weight. In a further embodiment the ratio of glucomannan to carbohydrate is about 20:80 by weight. In another embodiment the ratio of glucomannan to carbohydrate is about 15:85 by weight. In a further embodiment the ratio of glucomannan to carbohydrate is about 10:90 by weight. In another embodiment the ratio of glucomannan to carbohydrate is about 5:95 by weight. In a further embodiment the ratio of glucomannan to carbohydrate is about 1:99 by weight.

In a preferred embodiment the active agent comprises glucomannan and hyaluronic acid in a ratio of about 10:90 by weight. In another preferred embodiment the active agent comprises glucomannan and hyaluronic acid in a ratio of about 15:85 by weight. In a further preferred embodiment the active agent comprises glucomannan and hyaluronic acid in a ratio of about 20:80 by weight. In another preferred embodiment the active agent comprises glucomannan and hyaluronic acid in a ratio of about 25:75 by weight. In a further preferred embodiment the active agent comprises glucomannan and hyaluronic acid in a ratio of about 30:70 by weight.

In another preferred embodiment the active agent comprises glucomannan, hyaluronic acid and chitosan. In one embodiment the active agent comprises hyaluronic acid and chitosan in a ratio of from about 0.8:1.2 to about 1.2:0.8, eg,, a ratio of about 0.9:1.1, 1:1, 1.1:1, 1.2:1. In a preferred embodiment the ratio of hyaluronic acid to chitosan is approximately 0.9:1. Glucomannan may be present in an amount of about 10 to about 40 percent by weight, eg., 15 percent by weight, 20 percent by weight, 25 percent by weight, 30 percent by weight or 35 percent by weight. In a particularly embodiment the active agent comprises approximately 20 percent by weight glucomannan and hyaluronic acid and chitosan in a ratio of about 0.9:1.

Regeneration, wound healing and augmentation refer to changing the structure of the dermis or encouraging growth of new dermal tissue. These effects occur due to production of new collagen by cells in the dermis stimulated by the glucomannan oligosaccharide or polysaccharide according to the present invention. A regenerated and augmented dermis may give rise to skin which is less wrinkled, smoother in texture, firmer, plumper and/or more elastic. Regenerated aged skin may appear to be younger in appearance than untreated skin on the same individual. Regenerated wounded or burnt skin may heal more quickly than untreated skin.

The experimental results presented herein clearly demonstrate the potential of the present invention in improving skin characteristics. The present invention provides a clear and unexpected advance in the science of skin augmentation and regeneration as there are no known other agents which have a demonstrated ability to both attract fibroblasts and to stimulate production of collagen to such an extent in skin.

The treatment methods of the present invention may be carried out by application of a pharmaceutical formulation comprising the active agent, alone or in combination with another agent such as collagen or a carbohydrate (eg, hyaluronic acid) to an area of skin. Suitable formulations include, but are not limited to, topical creams, ointments, lotions, gels, films, parenteral formulations, masks, sheets, sponges or dermal scaffolds. In a preferred embodiment the glucomannan active agent is administered as a topical formulation. In another preferred embodiment the glucomannan active agent is administered as a parenteral (ie, injectable) formulation. Application of the formulation comprising glucomannan oligosaccharides or polysaccharides promotes fibroblast migration to or near the site of application and increases the production of collagen in the skin.

Injectable treatment regimes typically commence with a course of one or more treatments over a period of a few months with maintenance treatments performed less frequently. Following treatment in accordance with the present invention, skin showing signs of ageing may be smoother in texture, firmer, plumper, more elastic, less wrinkled, or a combination thereof. Following treatment in accordance with the present invention, wounded skin such as that resulting from trauma, burns, diabetic ulcers or decubitis ulcers, may heal more quickly than untreated skin.

In other embodiments, a treatment regime may comprise topical administration of a topical formulation to an area of skin to be treated. The topical formulation may be applied several times (eg, once, twice, three times) per day over a treatment period which may be 1, 2, 3, 6, 12 months, or longer. Topical formulations may be applied on consecutive days, alternate days or weekly. The treatment may be continuous or discontinuous. For example, treatment may continue for a period of time, then cease, then recommence at a later time. Appropriate treatment regimes may be readily determined by those skilled in the art.

In accordance with the present invention endogenous collagen may be produced at desired sites in the skin. In contrast, other known modes of treatment often require the addition of exogenous collagen, hyaluronic acid or synthetic materials to provide augmentation or remodelling of skin. Such modes of treatment have the serious disadvantage of using non-human animal derived collagen, particularly bovine collagen, which can be contaminated with infectious or deleterious agents, such as viruses or prions.

Topical formulations typically include 0.1% to saturation of glucomannan oligosaccharide or polysaccharide in a suitable carrier vehicle. Such vehicles are well known in the art and include encapsulation of the glucomannan oligosaccharide or polysaccharide in liposomes or other forms of micro-encapsulation or microfine (about 1 µm to 20 µm) particles of oligosaccharide or polysaccharide undissolved in an anhydrous vehicle as described, for example, in EP 0 572 494.

Many drugs or compositions are given as pro-drugs to increase absorption or delivery of the active agent. One form in this regard is to chemically modify the active agent to increase lipophilicity. Pro-drugs can be converted to the active drug in the body by specific or non-specific methods. For example, non-specific conversion of pro-drug to drug can be by hydrolysis. Specific conversion of pro-drug to drug can occur by enzymes. For example, esterase enzymes in the skin may be capable of cleaving palmitate moieties attached to carbohydrate sugars to increase lipophilicity.

Examples of methods suitable for use in modifying glucomannan oligosaccharide or polysaccharide compounds suitable for the present invention can be found in the literature. These include, but are not limited to, the attachment of lipid soluble moieties such as palmitate, or carboxymethylation. It will be appreciated, however, that other chemical modifications would also be suitable, depending on the type of modification required and the oligosaccharide or polysaccharide compound to be modified. Such modifications are known to those skilled in the art.

Injectable formulations typically may comprise the glucomannan oligosaccharide or polysaccharide in solution of water, saline, or other physiologically suitable diluent.

Other suitable formulations in accordance with the present invention include combination or cross-linking of the glucomannan oligosaccharide or polysaccharide with other materials used for soft tissue augmentation, such as collagen or hyaluronic acid, including cross-linked hyaluronic acid. The latter may provide the benefit of immediate soft tissue augmentation provided by the collagen or crosslinked hyaluronic acid with the longer term effects of the glucomannan oligosaccharide or polysaccharide.

The pharmaceutical forms suitable for injection include sterile aqueous solutions and sterile powders for the extemporaneous preparation of sterile injectable solutions or dispersion. The form should be sterile and must be fluid to the extent that easy syringability exists. It must be stable under the conditions of manufacture and storage and can be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about, by various antibacterial and antifungal agents, for example, parabens, chlorobutanol, phenol, sorbic acid and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions may be prepared by incorporating the active agent in the required amount in the appropriate solvent with various of the other ingredients enumerated above, as required, followed by sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It can be advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired effect in association with the required pharmaceutical carrier or diluent. The specification for the novel dosage unit forms of the invention can be dictated by and directly dependent on (a) any unique characteristics of the active material and the particular effect to be achieved, and (b) any limitations inherent in the art of compounding such an active material for the treatment of disease in living subjects having a diseased condition in which bodily health is impaired as herein disclosed in detail.

For topical applications, suitable diluents and cream, lotion, ointment, gel, mask, film and sheet bases are well known to the art and may be applicable for use in the present invention.

EXAMPLES

The following examples are illustrative of the invention and of the beneficial effects which can be achieved with the compositions of the invention and should not be construed as limiting.

Example 1

Preparation of 10% Soluble Glucomannan Solution.

A standardised solution of hydrochloric acid (7.5% v/w; 240 mL) was added to glucomannan (Wako, Glucomannan from Konjac; 10.12 g) forming an extremely viscous mixture. Additional demineralised water (20 mL) was added to the glucomannan mixture in order to maintain it at a fluid level. The solution was shaken vigorously several times a day over 192 hours and during this time further portions of demineralised water (total of 240 mL) were added to maintain the glucomannan mixture at a fluid level as it slowly turned into a jelly-like consistency. After 192 hours the acid treated glucomannan was neutralized with the addition of a standardised solution of sodium hydroxide (10%, w/v). Attempts were directed at redissolving the hydrolysed glucomannan solid into demineralised water (50 mL) but residual solid persisted. The resulting mixture was heated gently and sonicated for several minutes to dissolve this solid material. Any residual insoluble material was removed by passing the mixture through a 0.45 μm filter membrane. The resulting filtrate was freeze-dried to remove excess water. The resulting solid was redissolved successfully in demineralised water (20 mL) and passed through a size exclusion column (Sephadex 15; 5 g, 20×60 mm). The resulting purified fractions were combined and freeze-dried furnishing salt-free hydrolysed glucomannan (2.6906 g).

Hydrolysed glucomannan (2.6906 g) was dissolved in normal saline solution (27 mL) to give a 10% solution.

Example 2

Evaluation of the effects of glucomannan after injection into human skin explants. Evaluations of the cellular effects were examined using immunohistology procedures.

Materials and Methods

In vitro percutaneous absorption testing procedures using modifications of the OECD (Organisation for Economic Co-operation and Development) Test guideline 428 (2004): Skin Absorption: in vitro method and relevant publications (Diembeck et al., 1999; Walters et al. 1997) were used. The methodologies for in vitro percutaneous absorption, immunohistochemistry and histopathology are well known in the art.

Procedures

The assay is summarised as follows. (For further detail refer to Hayes and Markovic 2002). Percutaneous absorption studies were performed using a Franz cell diffusion system (Crown Glass Co., New Jersey, USA) consisting of nine vertical glass diffusion cells (2.5 cm diameter) with flat ground glass O ring joints. Each diffusion cell was mounted on a PermeGear stainless steel vertical cell stirrer with water bath re-circulator.

Freshly excised full thickness human abdominal skin was obtained from patients undergoing surgical resection (Eastern Suburbs Private Hospital, Randwick), collected in a saline solution HBSS (Hanks Balanced Salt Solution, Invitrogen) and immediately transported to CSAT laboratories (UNSW Human Research Ethics Committee Approval HREC 04004: Assessment of in vitro percutaneous absorption of topical preparations using skin biopsies). Skin was washed thoroughly with sterile colour free DMEM/F12 (Dulbecco's Modified Eagle Medium/HamsF12, Invitrogen) to remove surface debris. The subcutaneous fat layer was removed by gross dissection. Circles of full-thickness skin, 2.5 cm in diameter (4.9 $cm^2$ in surface area), were cut using a sharpened stainless steel cork borer and surgical scissors.

Skin circles were placed epidermis side up on each of the diffusion cells between two clamped ground glass joints, and allowed to equilibrate for approximately 30 minutes. Prior to the placement of skin circles, receptor chambers of the diffusion cells were filled (mean volume 15.0 ml) with colour-free DMEM/F12+1% (v/v) of antibiotic (200 mM L-glutamine, 10.000 units penicillin, 10 mg streptomycin per ml: Sigma, USA) and stirred constantly using a mini magnetic stirrer. The temperature of the jacketed diffusion cells was regulated by water thermostat maintained at 34° C.±1° C.

Test Compounds

Soluble glucomannan solution was prepared as in Example 1.

TABLE 1

Starch Solutions and Control Test Preparations

| Name | Preparation |
| --- | --- |
| Hydrolysed Glucomannan | 10% solution in normal saline |
| Blank | Untreated |
| Physiological Saline 0.9% | Baxter Healthcare |
| Starch (Amylopectin) | 1.5% in normal saline |
| Hydrolysed Yeast Mannan | 9% in normal saline |

Exposure and Doses

Aliquots (100 µl) of glucomannan solution (and saline control, starch and mannan preparations, respectively) were intradermally injected (in duplicate) to skin discs using a 27 gauge needle (Becton Dickinson). The skin was then occluded with paraffin and a watch glass placed over each of the ground glass joints. A 48 hour exposure period was used.

Dissection of Skin Disc

At the completion of the exposure period the surface of each treated and control skin disc was swabbed using a cotton bud and removed from the Franz cell. Excess untreated skin from the circumference was removed. One half was placed in aluminium foil and frozen while the second half was stored in Buffered Formalin (4% formaldehyde in PBS) for 48 hr.

Procedure

The detailed procedure has been published previously (Markovic et al., 1994; 1995). The procedure is summarised as follows. Following the percutaneous absorption experiment, the skin discs were frozen and used for immunohistochemical analysis. Frozen sections were processed into cryoblocks (stored at −70° C.) using a Reichert Jung Cryocut 1800. Tissue sections were cut from each block and placed on coated slides for immunohistochemical preparation.

Immunohistochemical Analysis

Paraffin coated slides were labelled and heated in an oven at 70° C. for five minutes. Slides were washed in the following solvents for a minimum of 2 minutes each: (i) Xylene (3 changes), (ii) 100% Ethanol (2 changes), (iii) 95% Ethanol (1 change), (iv) 80% Ethanol (1 change), (v) Water (1 change), and (vi) 1×PBS (2 changes) and decanted. Frozen coated slides were thawed at room temperature, fixed for 1 minute in acetone/methanol and air dried.

All slides were blocked for non-specific binding sites for antibodies by the addition of 100 µl of 2% (w/v) BSA (bovine serum albumin; Trace) in HBSS, to each slide for 15 minutes. The slides were then decanted and 100 µl of the desired primary antibody) was added. These included:

Anti-Human Collagen Type I Antibody (Chemical Credential, ICN)
  a) Gomori stain for total collagens
  b) Anti-Human Fibroblast clone 5B5 (DakoCytomation)
  c) HLA-DR for activated macrophages All antibodies were diluted according to manufacturers' specifications in HBSS containing 1% (w/v) BSA, added to each slide and left at room temperature for 30 minutes. The antibody was decanted and slides were washed four times with PBS (Phosphate buffered Saline) containing 0.05% (v/v) Triton X-100. The secondary antibodies were diluted (1:100) and applied in the same manner as the primary antibodies. Following a 30 minute exposure, slides were washed four times in PBS with 0.05% Triton X-100 and then placed in TBS Buffer 1 for 5 minutes.

Detection

Slides were decanted and biotin on the bound secondary antibody was detected using a single application of streptavidin-biotinylated alkaline phosphatase (DakoCytomation) diluted (1:100) in TBS Buffer 1. Slides were washed four times in TBS Buffer 1, incubated in TBS Buffer 2 for 5 minutes, and decanted.

Visualisation

Naphthol AS/MX phosphate/fast red substrate (100 µl) containing 5 mM (1.20 g/L of distilled water) levamisole (Sigma) was added to each section and left at room temperature for 20-40 minutes. The colour development was assessed periodically by microscopic examination (Leitz Laborlux 12 Pol). Once optimal colour development was achieved usually 20 minutes (with no colour development in the controls), slides were washed as follows: twice in TBS Buffer 2; once by tap water; twice in TBS Buffer 2 and once by tap water.

Slides were counter stained with filtered Mayer's Haematoxylin for approximately 2 minutes. Slides were then washed as follows: tap water 2 washes (to remove excess stain); dilute ammonium solution for 30 seconds and tap water 2 washes.

Results a) Anti-Human Collagen Type I Antibody (Chemical Credential, ICN).

Figure 7:
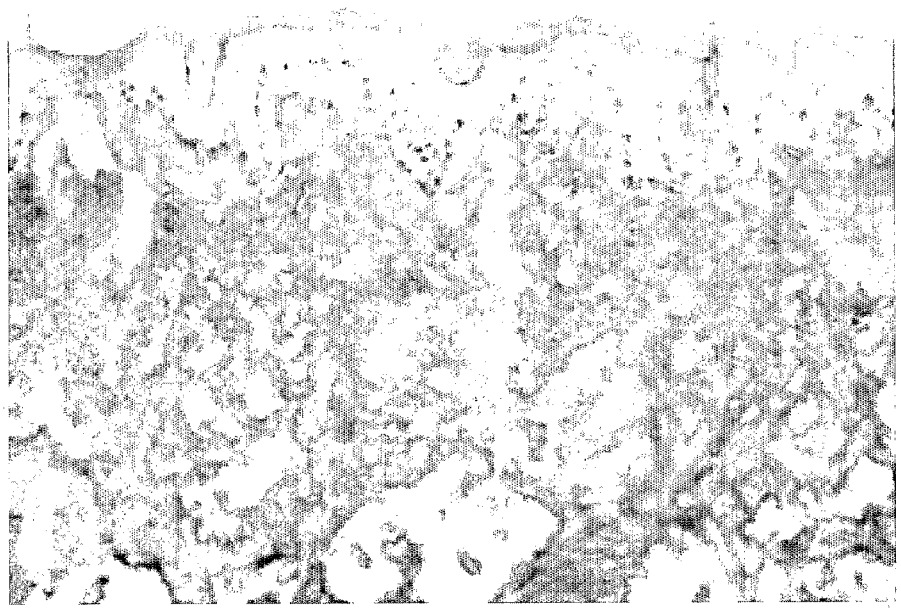
FIG. 7 shows histological sections of Collagen I stained human skin (A) 48 hours after intradermal injection of Saline (control), magnification ×200; (B) increased collagen 48 hours after intradermal injection of glucomannan.
Figure 7:
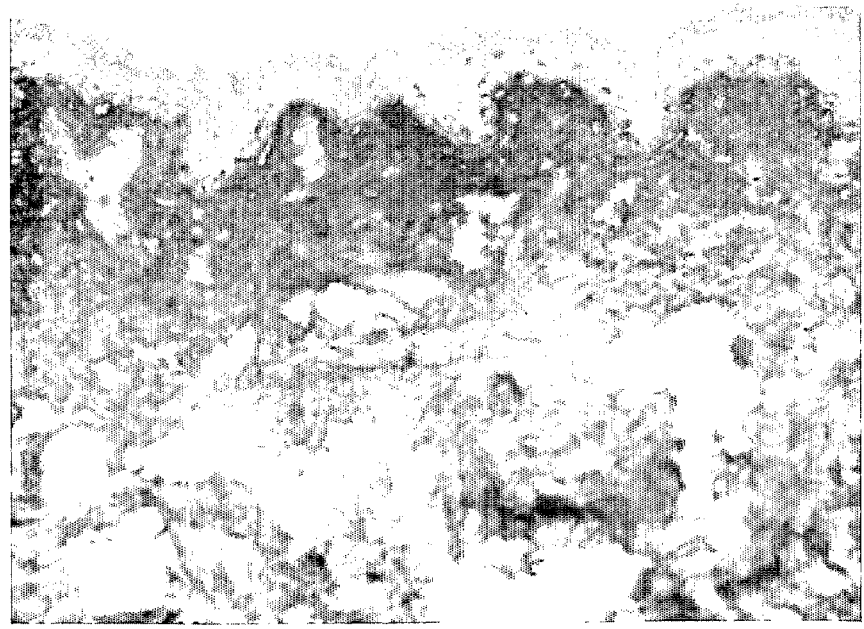
Figure 8:
FIG. 8 shows histological sections of Collagen I stained human skin (A) 48 hours after intradermal injection of Saline (control), magnification ×32; (B) 48 hours after intradermal injection of starch is similar to control.
Figure 8:
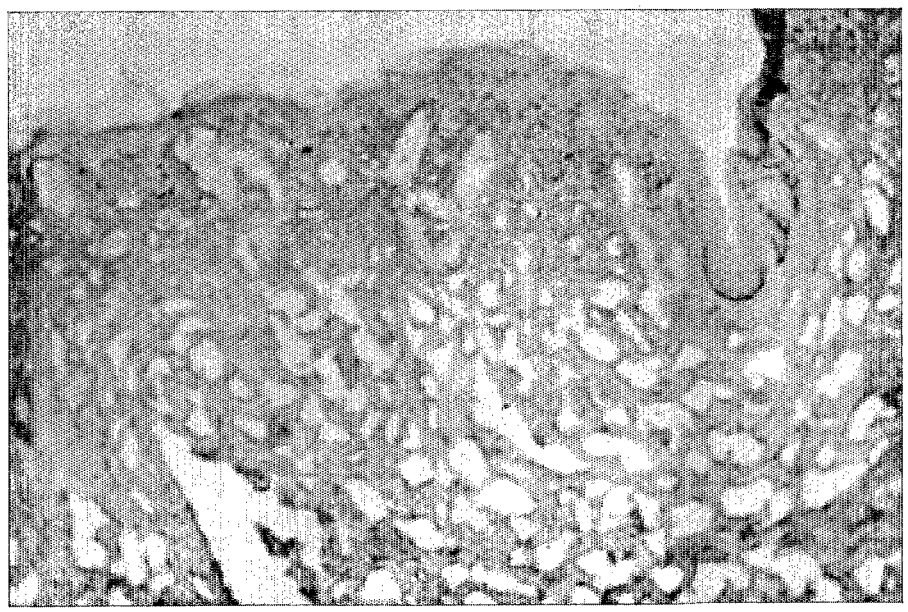
Figure 9:
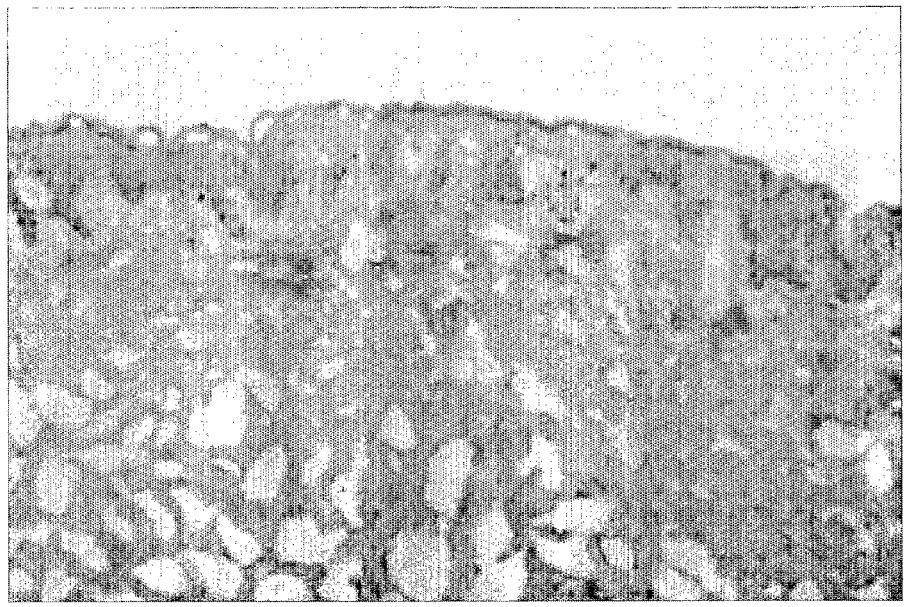
FIG. 9 shows histological sections of Collagen I stained human skin (A) 48 hours after intradermal injection of Saline (control), magnification ×32; (B) 48 hours after intradermal injection of mannan is similar to control.
Figure 9:
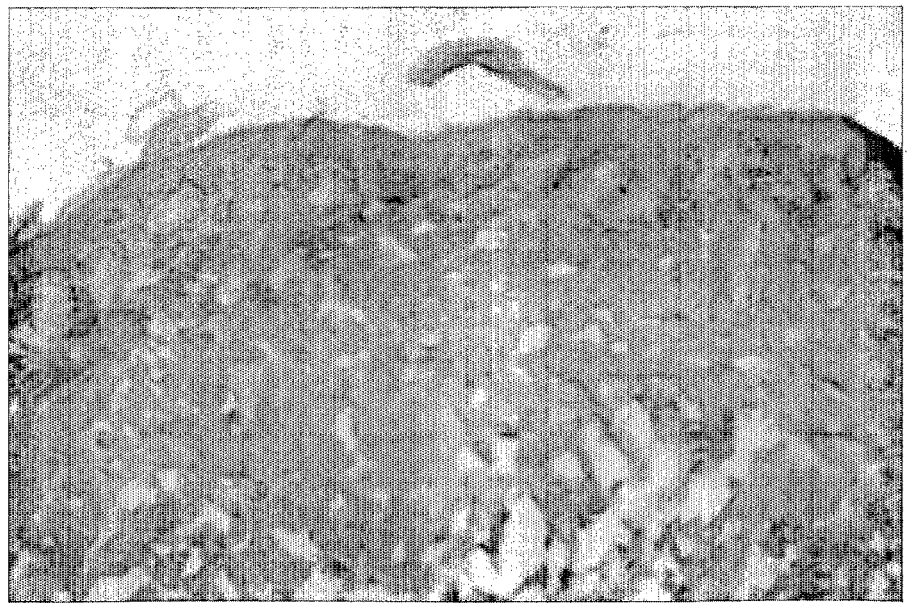

After 48 hours skin treated with glucomannan showed markedly increased dermal collagen I compared to control (FIGS. 1, 7). Dermal collagen I in skin treated with starch (FIG. 8) or mannan (FIG. 9) was similar to the control.

b) Gomori stain for total collagens.

Figure 2:
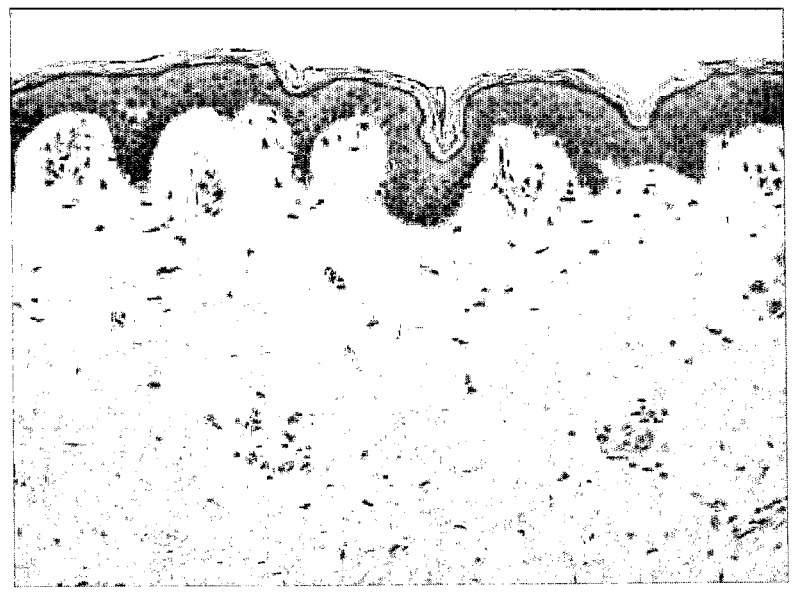
FIG. 2 shows histological sections of human skin from Example 2, Gomori's stain (A), showing an increase in total collagens 48 hours after intradermal injection of glucomannan (B).
Figure 2:
Figure 5:
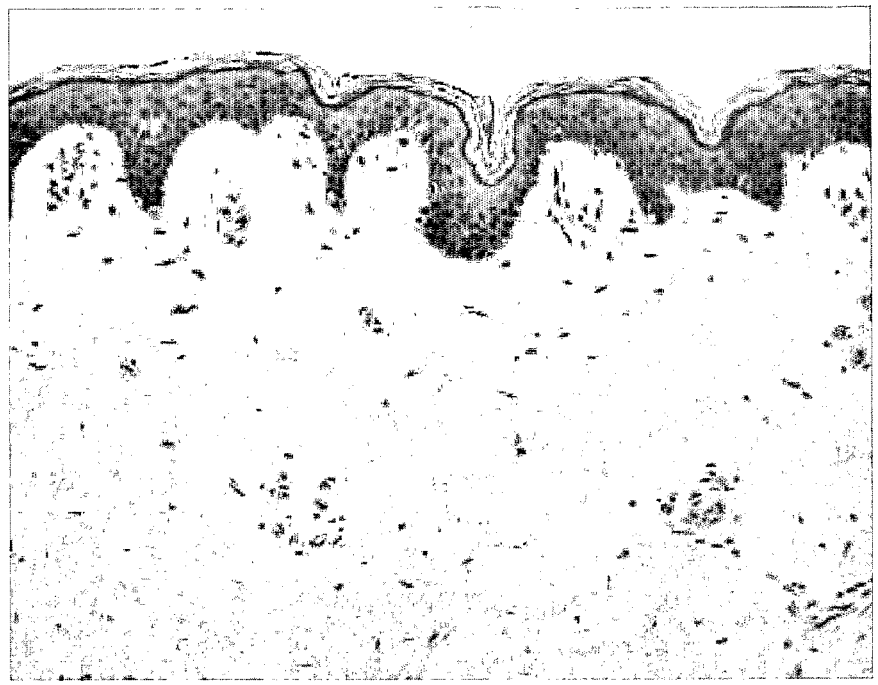
FIG. 5 shows histological sections of human skin Gomori's stain (A) total collagen 48 hours after intradermal injection of Saline (control); (B) total collagen 48 hours after intradermal injection of starch collagen is similar to control.
Figure 5:
Figure 6:
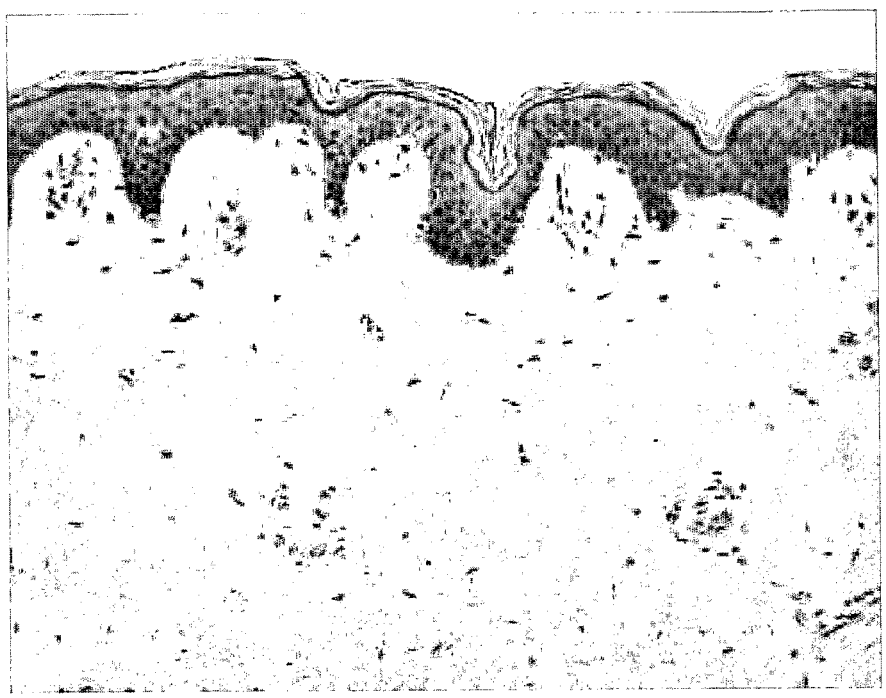
FIG. 6 shows histological sections of human skin Gomori's stain (A) total collagen 48 hours after intradermal injection of Saline (control); (B) total collagen 48 hours after intradermal injection of mannan is similar to control.
Figure 6:

After 48 hours skin treated with glucomannan showed markedly increased total dermal collagen compared to control (FIG. 2). In contrast, after 48 hours skin treated with starch (FIG. 5) or mannan (FIG. 6) showed dermal collagen levels similar to the control.

c) Anti-Human Fibroblast clone 5B5 (DakoCytomation).

Figure 3:
FIG. 3 shows histological sections of human skin from Example 2, anti-human fibroblast clone 5B5 stain (DakoCytomation) stain (A), showing an increase in fibroblast numbers 48 hours after intradermal injection of glucomannan (B).
Figure 3:
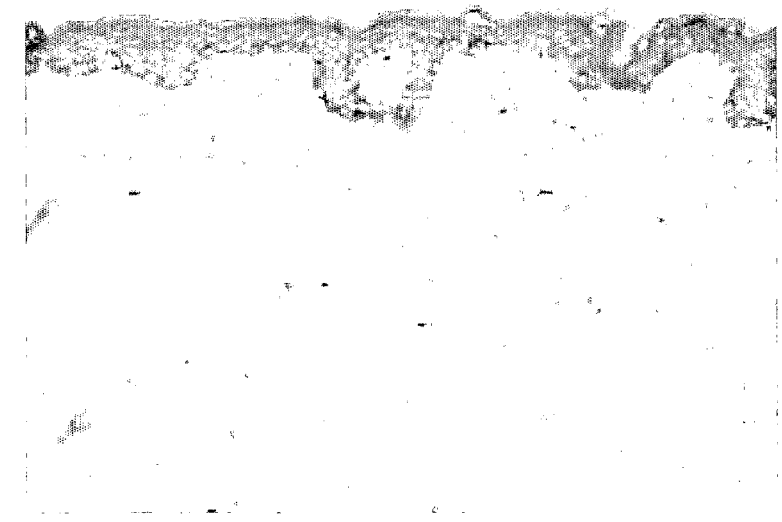
Figure 10:
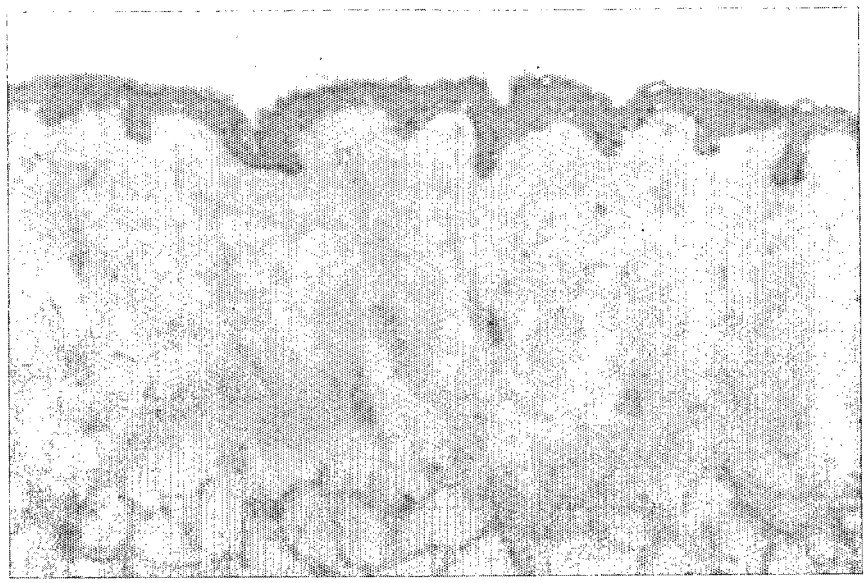
FIG. 10 shows histological sections of human skin, anti-human fibroblast clone 5B5 stain (DakoCytomation) stain (A), 48 hours after intradermal injection of Saline (control), magnification ×32; (B) 48 hours after intradermal injection of mannancollagen fibroblast numbers are similar to control.
Figure 10:
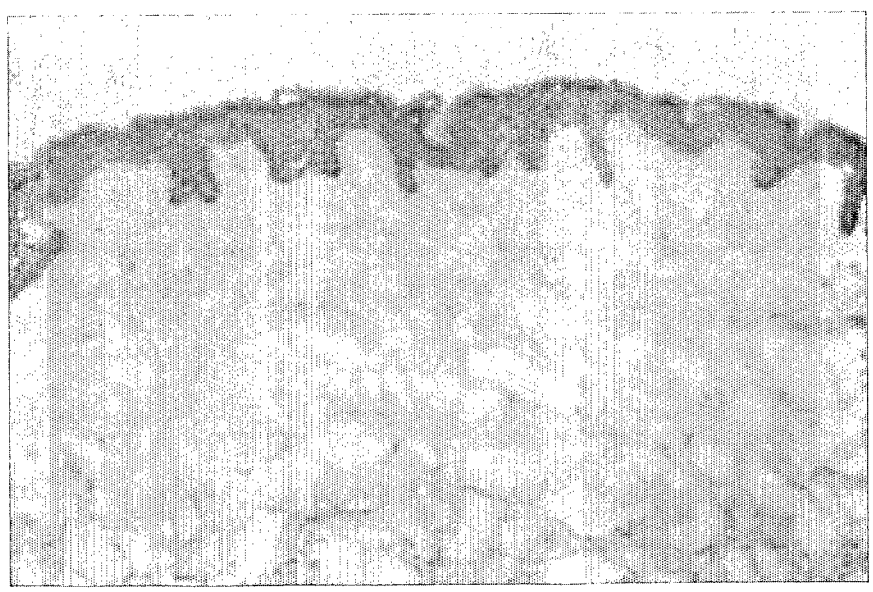

After 48 hours skin treated with glucomannan showed markedly increased numbers of fibroblasts compared to control (FIG. 3). In contrast, after 48 hours skin treated with mannan (FIG. 10) showed similar numbers of fibroblasts to the control.

d) HLA-DR for activated macrophages.

Figure 4:
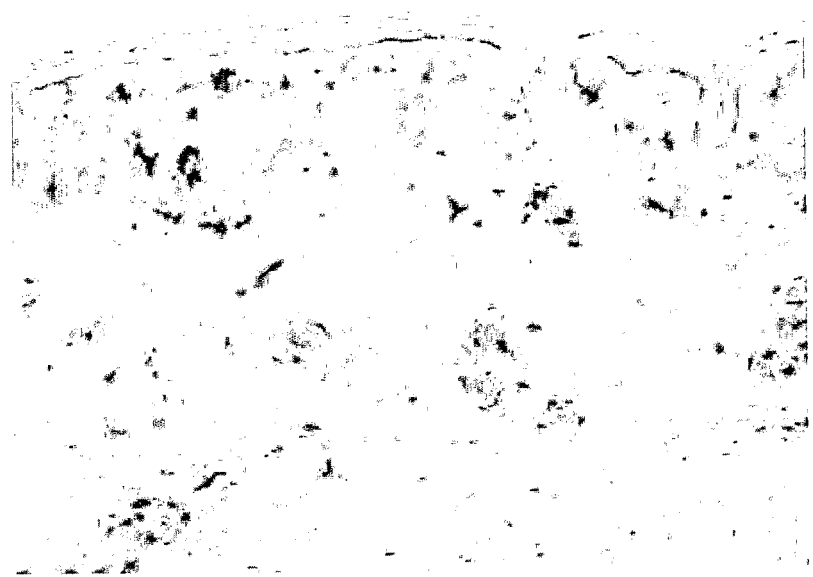
FIG. 4 shows histological sections of human skin from Example 2, HLA-DR stain (A), showing an increase in activated macrophage numbers 48 hours after intradermal injection of glucomannan (B).
Figure 4:
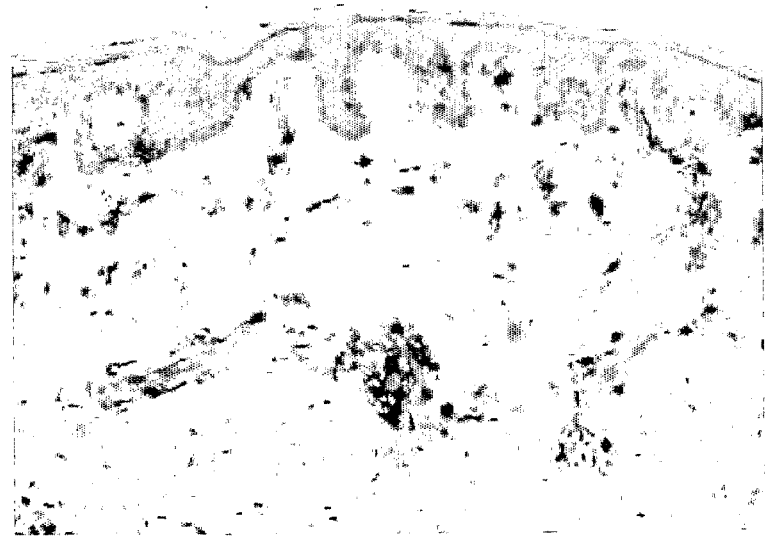

After 48 hours skin treated with glucomannan showed increased numbers of macrophages compared to control (FIG. 4).

Example 3

Investigation of the efficacy of a novel dermal filler, Hyaluronic acid/Glucomannan (HA/GM gel) ('test item') compared with an existing product, Restylane™ gel.

Definitions

Dermal irritation is indicated by signs of redness and/or swelling of the skin at the test site following application of a test item.

Dose is the amount of the test item administered. Dose is expressed as weight (g, mg) or as weight/weight of test animal (eg, mg/kg).

Test item is the article that is the subject of the study, i.e., Hyaluronic acid/Glucomannan gel (HA/GM gel; 85:15 by weight).

Methodology

The test item was injected intradermally as a single dose of 100 µL into the dorsal dermis of the left ear of each of the 15 experimental rabbits. The right ear of each rabbit was injected intradermally with Restylane™ gel and served as the control for comparative purposes.

Body weights were determined weekly throughout the study. Observations of skin irritation/intradermal distension at the injection site (weekly) and clinical effects (daily) were made throughout the experimental period.

Groups of five animals were sacrificed after 1, 2 and 3 months (Days 29, 57 and 85, respectively). The injection sites from each animal were preserved in formalin and embedded in paraffin using standard histological procedures. The sections were cut serially, perpendicular to the skin surface (four sections of each tissue). Prior to histological examination the sections were stained with Haematoxylin and Eosin (H&E) for the shape and texture of injected material, Alcian blue stain and toluidine blue stain for hyaluronic acid and Masson's trichrome stain for collagen.

Efficacy of the test item was assessed by measurement of intradermal distension and proliferation of collagen within the dermis.

Test Item

| Identification | Batch No. | Physical description | Storage | Manufacturer |
|---|---|---|---|---|
| Hyaluronic acid/ Glucomannan gel (HA/GM gel; 85:15 by weight) | 1 | Clear gel | Room temperature | Ultraceuticals Pty Ltd, Australia |

The HA/GM gel was supplied in 15 syringes with sterile needles attached. One syringe was used for each animal. The HA/GM gel comprised 85% hyaluronate and 15% glucomannan by weight cross-linked with the chemical cross-linking agent butanediol diglycidyl ether.

Control Item

| Identification | Batch No. | Physical description | Storage | Manufacturer |
|---|---|---|---|---|
| Restylane ™ gel | 9310-3 | Clear gel | Room temperature | Q-Med AB, Sweden |

The Restylane™ gel in was provided in 10 syringes with sterile needles attached. A total of six syringes was used for the fifteen animals.

Animals

Species and Strain

A total of 15 young adult female New Zealand White (NZW) rabbits, weighing between 1.8 and 2.5 kg at receipt, were used for the test. The animals were sourced from Nanowie Small Animal Production Unit, Belbrae, VIC, Australia. The animals were acclimatised to the laboratory conditions for at least 5 days before commencement of the study. All animals were examined during the acclimatisation period to confirm suitability for the study. The rabbits were housed in cages in groups of 2 or 3 during the experimental period.

Treatment Allocation

Three groups of 5 female rabbits were allocated to treatment groups without bias as follows:

TABLE 2

Animal Allocation

| Group | No. of Animals | Unique animal ref | Test item/ Control item | Dose | Days of observation |
|---|---|---|---|---|---|
| 1 | 5 | L066-L070 | left ear: HA/GM gel | 0.1 mL | 28 |
|   |   |   | Right ear: Restylane gel | 0.1 mL |   |
| 2 | 5 | L071-L075 | Left ear: HA/GM gel | 0.1 mL | 56 |
|   |   |   | Right ear: Restylane gel | 0.1 mL |   |
| 3 | 5 | L076-L080 | Left ear: HA/GM gel | 0.1 mL | 84 |
|   |   |   | Right ear: Restylane gel | 0.1 mL |   |

Feed and Water

The rabbits were fed on a diet of Rabbit & Guinea pig pellets (Gordon's Specialty Stock Feeds DOM: 6 Feb. 2008) and provided with tap water ad libitum. Water was analysed routinely for bacterial contaminants and there were no contaminants found that could have interfered with the conduct of the study.

Environment

Environmental controls for the animal room were set to maintain a temperature of 22±3° C. and a relative humidity between 30 and 70%. The automated light/dark cycle was 12 hours light/12 hours dark.

Procedure

A dose of 100 µL of the HA/GM gel was injected intradermally in the dorsal dermis of the left ear and 100 µL of Restylane™ gel was injected intradermally in the dorsal dermis of the right ear of each rabbit. The injection caused a dome-shaped bleb that was easily palpated. The locations of the injected sites were identified and the type of material injected were marked on the ear and on a transparent plastic sheet placed over the ear for later identification.

Observation of Animal

Body weights—Body weights were determined weekly throughout the study.

Skin irritation assessment—Animals were examined for signs of erythema and oedema weekly. Skin irritation reactions were graded according to the scale described in Tables 3 and 4.

TABLE 3

Evaluation of skin reactions (Draize et al, 1944)

|   | Score |
|---|---|
| ERYTHEMA AND ESCHAR FORMATION |   |
| No erythema | 0 |
| Very slight erythema (barely perceptible) | 1 |
| Well defined erythema | 2 |
| Moderate to severe erythema | 3 |
| Severe erythema (beet redness) to eschar formation to preventing grading of erythema | 4 |
| OEDEMA FORMATION |   |
| No oedema | 0 |
| Very slight oedema (barely perceptible) | 1 |
| Slight oedema (edges of area well defined by definite raising) | 2 |
| Moderate oedema (area raised approx. 1 mm) | 3 |
| Severe oedema (raised more than 1 mm and extending beyond area of exposure | 4 |
| Maximum Score for Primary Irritation | 8 |

TABLE 4

| Irritation Index (Draize et al. 1944) | |
|---|---|
| Score | Observed effect |
| 0 | non-irritant |
| 0-0.5 | minimal irritant |
| 0.5-2 | mild irritant |
| 2-5 | moderate irritant |
| 5-8 | severe irritant |

Intradermal Distension and Scoring

The injection sites were examined for intradermal distension. Intradermal distension was graded according to an in-house scale described in Table 5A.

TABLE 5A

| Intradermal distension scores | |
|---|---|
| Score | Observed effect |
| 1 | barely perceptible |
| 2 | mildly perceptible |
| 3 | well defined |

Clinical Observations

The animals were observed daily. Particular care was taken to look for signs of toxicity and abnormal behaviour. Skin and fur, eyes and mucous membranes, respirator, circulatory, autonomic and central nervous systems, somatomotor activity and behaviour patterns were monitored. Particular attention was paid to observation of tremor, convulsion, salivation, diarrhoea, lethargy, sleep and coma.

Sacrifice

All animals from Groups 1, 2 and 3 were sacrificed on Days 29, 57 and 85, respectively. The injection sites from both ears of each animal were dissected and preserved in 10% buffered formalin.

Slide Preparation and Histopathology

Surgical & Orthopaedic Research Laboratories of the Prince of Wales Hospital, Randwick NSW, Australia processed the slides for histopathology. Representative sections of the tissues were placed in labelled cassettes. Cassettes were placed in an automated tissue processor and taken through several stages of alcohol dehydration, solvent clearing and wax infiltration. Infiltrated tissues were embedded in wax blocs, which were sectioned on a microtome at 5 µm. The sections were cut serially, perpendicular to the skin surface. Four section were made for each tissue. The sections were placed on pre-labelled glass slides and stained as follows: Haematotoxylin and Eosin (H&E) were used for routine histological evaluation, Masson's trichrome stained sections were used for visualisation of hyaluronic acid and Alcian blue stained sections were used for the confirmation of hyaluronic acid. Stained sections were dehydrated, then solvent cleared and cover slipped.

Histopathology

Histopathological examinations of the injection sites were performed on all animals in all groups. Slides were evaluated for histopathological changes under light microscopy at a magnification of 100 to 1000 times.

The severity of the histologic lesions was graded according to a scale devised by the histopathologist in Table 5B.

TABLE 5B

| Severity of histologic lesion scores | |
|---|---|
| Score | Observation |
| 0 | normal |
| 1 | minimal change |
| 2 | mild change |
| 3 | moderate change |
| 4 | severe change |

The maximum dimensions of the injection site were determined on the H&E stained sections using an ocular micrometer (Olympus stage micrometer and Olympus OSM205798 eyepiece). A graduated scale was located within one eyepiece and was calibrated against a stage micrometer. Precise measurement of the maximum vertical and horizontal dimensions of the HA/GM gel and Restylane™ gel sites was not possible due to dispersal of the gel in the deep dermis, such that most of the gel occupied a main cavity and numerous smaller cavities surrounding the main cavity. For this reason two maximum vertical dimensions were measured: (a) the main cavity occupied by the gel; and (b) all cavities occupied by the gel (i.e., the distance from the most superficial aspect of the smaller cavities, through the main cavity, to the deepest aspect of the smaller cavities). The maximum horizontal dimension measured was of all cavities occupied by the gel. An individual comparison of all findings of the left ear (treated with HA/GM gel) and the right ear (treated with Restylane™ gel) was made for each animal.

Statistical Analysis

Means and standard deviations were determined for each parameter analysed. Clinical observations were summarised by descriptive analysis.

Results and Discussion

Mortality

No mortalities occurred during the study.

Body Weights

Summarised data are presented in Table 6.

TABLE 6

| | Mean body weights (kg) | | |
|---|---|---|---|
| | Mean ± SD (n = 5) | | |
| Day | Group 1 L066-L070 | Group 2 L071-L075 | Group 3 L076-L080 |
| 1 | 2.06 ± 0.12 | 2.40 ± 0.07 | 2.42 ± 0.18 |
| 8 | 2.23 ± 0.10 | 2.70 ± 0.14 | 2.64 ± 0.16 |
| 15 | 2.48 ± 0.10 | 2.88 ± 0.15 | 2.88 ± 0.19 |
| 22 | 2.60 ± 0.06 | 3.02 ± 0.17 | 3.06 ± 0.21 |
| 29 | 2.82 ± 0.08 | 3.24 ± 0.21 | 3.28 ± 0.23 |
| 36 | — | 3.42 ± 0.25 | 3.47 ± 0.23 |
| 43 | — | 3.58 ± 0.20 | 3.61 ± 0.23 |
| 50 | — | 3.71 ± 0.22 | 3.78 ± 0.25 |
| 57 | — | 3.89 ± 0.31 | 3.94 ± 0.28 |
| 64 | — | — | 4.11 ± 0.29 |
| 71 | — | — | 4.21 ± 0.28 |
| 78 | — | — | 4.29 ± 0.34 |
| 85 | — | — | 4.39 ± 0.36 |

Notes:
SD, standard deviation

No significant weight loss was observed in any of the animals (Group 1-3) during the experimental period.

Clinical Observations

Summarised data are presented in Table 7.

TABLE 7

Summarised clinical observations

Group/Animal number (n = 5)

| Day | Group 1<br>L066-L070 | Group 2<br>L071-L075 | Group 3<br>L076-L080 |
|---|---|---|---|
| 1-7 | NA | NA | NA |
| 8-14 | NA | NA | NA |
| 15-21 | NA | NA | NA |
| 22-29 | NA | NA | NA |
| 30-35 | — | NA | NA |
| 36-42 | — | NA | NA |
| 43-49 | — | NA | NA |
| 50-57 | — | NA | NA |
| 58-63 | — | — | NA |
| 64-70 | — | — | NA |
| 71-77 | — | — | NA |
| 78-85 | — | — | NA |

Notes:
NA, no abnormalities

There were no clinical abnormalities observed throughout the 28-day experimental period for Group 1 (Day 29), Group 2 (Day 57) or Group 3 (Day 85).

Dermal Irritation/Intradermal Distension Assessment

Individual dermal irritation scores are presented in Tables 8-10. Mean values are presented in Table 11.

TABLE 8A

Individual skin irritation scores of Group 1 treated with HA/GM gel

| | | Animal number | | | | |
|---|---|---|---|---|---|---|
| Day | Skin reaction | L066 | L067 | L068 | L069 | L070 |
| 8 | Erythema | 0 | 0 | 0 | 0 | 0 |
|   | Oedema | 0 | 0 | 0 | 0 | 0 |
| 15 | Erythema | 0 | 0 | 0 | 0 | 0 |
|   | Oedema | 0 | 0 | 0 | 0 | 0 |
| 22 | Erythema | 0 | 0 | 0 | 0 | 0 |
|   | Oedema | 0 | 0 | 0 | 0 | 0 |
| 29 | Erythema | 0 | 0 | 0 | 0 | 0 |
|   | Oedema | 0 | 0 | 0 | 0 | 0 |

Note:
refer to Table 3 for scoring scales.

TABLE 8B

Individual skin irritation scores of Group 1 treated with Restylane™ gel

| | | Animal number | | | | |
|---|---|---|---|---|---|---|
| Day | Skin reaction | L066 | L067 | L068 | L069 | L070 |
| 8 | Erythema | 0 | 0 | 0 | 0 | 0 |
|   | Oedema | 0 | 0 | 0 | 0 | 0 |
| 15 | Erythema | 0 | 0 | 0 | 0 | 0 |
|   | Oedema | 0 | 0 | 0 | 0 | 0 |
| 22 | Erythema | 0 | 0 | 0 | 0 | 0 |
|   | Oedema | 0 | 0 | 0 | 0 | 0 |
| 29 | Erythema | 0 | 0 | 0 | 0 | 0 |
|   | Oedema | 0 | 0 | 0 | 0 | 0 |

Note:
refer to Table 3 for scoring scales.

TABLE 9A

Individual skin irritation scores of Group 2 treated with HA/GM gel

| | | Animal number | | | | |
|---|---|---|---|---|---|---|
| Day | Skin reaction | L071 | L072 | L073 | L074 | L075 |
| 8 | Erythema | 0 | 0 | 0 | 0 | 0 |
|   | Oedema | 0 | 0 | 0 | 0 | 0 |
| 15 | Erythema | 0 | 0 | 0 | 0 | 0 |
|   | Oedema | 0 | 0 | 0 | 0 | 0 |
| 22 | Erythema | 0 | 0 | 0 | 0 | 0 |
|   | Oedema | 0 | 0 | 0 | 0 | 0 |
| 29 | Erythema | 0 | 0 | 0 | 0 | 0 |
|   | Oedema | 0 | 0 | 0 | 0 | 0 |
| 36 | Erythema | 0 | 0 | 0 | 0 | 0 |
|   | Oedema | 0 | 0 | 0 | 0 | 0 |
| 43 | Erythema | 0 | 0 | 0 | 0 | 0 |
|   | Oedema | 0 | 0 | 0 | 0 | 0 |
| 50 | Erythema | 0 | 0 | 0 | 0 | 0 |
|   | Oedema | 0 | 0 | 0 | 0 | 0 |
| 57 | Erythema | 0 | 0 | 0 | 0 | 0 |
|   | Oedema | 0 | 0 | 0 | 0 | 0 |

Note:
refer to Table 3 for scoring scales.

TABLE 9B

Individual skin irritation scores of Group 2 treated with Restylane™ gel

| | | Animal number | | | | |
|---|---|---|---|---|---|---|
| Day | Skin reaction | L071 | L072 | L073 | L074 | L075 |
| 8 | Erythema | 0 | 0 | 0 | 0 | 0 |
|   | Oedema | 0 | 0 | 0 | 0 | 0 |
| 15 | Erythema | 0 | 0 | 0 | 0 | 0 |
|   | Oedema | 0 | 0 | 0 | 0 | 0 |
| 22 | Erythema | 0 | 0 | 0 | 0 | 0 |
|   | Oedema | 0 | 0 | 0 | 0 | 0 |
| 29 | Erythema | 0 | 0 | 0 | 0 | 0 |
|   | Oedema | 0 | 0 | 0 | 0 | 0 |
| 36 | Erythema | 0 | 0 | 0 | 0 | 0 |
|   | Oedema | 0 | 0 | 0 | 0 | 0 |
| 43 | Erythema | 0 | 0 | 0 | 0 | 0 |
|   | Oedema | 0 | 0 | 0 | 0 | 0 |
| 50 | Erythema | 0 | 0 | 0 | 0 | 0 |
|   | Oedema | 0 | 0 | 0 | 0 | 0 |
| 57 | Erythema | 0 | 0 | 0 | 0 | 0 |
|   | Oedema | 0 | 0 | 0 | 0 | 0 |

Note:
refer to Table 3 for scoring scales.

TABLE 10A

Individual skin irritation scores of Group 3 treated with HA/GM gel

| | | Animal number | | | | |
|---|---|---|---|---|---|---|
| Day | Skin reaction | L076 | L077 | L078 | L079 | L080 |
| 8 | Erythema | 0 | 0 | 0 | 0 | 0 |
|   | Oedema | 0 | 0 | 0 | 0 | 0 |
| 15 | Erythema | 0 | 0 | 0 | 0 | 0 |
|   | Oedema | 0 | 0 | 0 | 0 | 0 |
| 22 | Erythema | 0 | 0 | 0 | 0 | 0 |
|   | Oedema | 0 | 0 | 0 | 0 | 0 |
| 29 | Erythema | 0 | 0 | 0 | 0 | 0 |
|   | Oedema | 0 | 0 | 0 | 0 | 0 |
| 36 | Erythema | 0 | 0 | 0 | 0 | 0 |
|   | Oedema | 0 | 0 | 0 | 0 | 0 |
| 43 | Erythema | 0 | 0 | 0 | 0 | 0 |
|   | Oedema | 0 | 0 | 0 | 0 | 0 |

TABLE 10A-continued

Individual skin irritation scores
of Group 3 treated with HA/GM gel

| | | Animal number | | | | |
|---|---|---|---|---|---|---|
| Day | Skin reaction | L076 | L077 | L078 | L079 | L080 |
| 50 | Erythema | 0 | 0 | 0 | 0 | 0 |
| | Oedema | 0 | 0 | 0 | 0 | 0 |
| 57 | Erythema | 0 | 0 | 0 | 0 | 0 |
| | Oedema | 0 | 0 | 0 | 0 | 0 |
| 64 | Erythema | 0 | 0 | 0 | 0 | 0 |
| | Oedema | 0 | 0 | 0 | 0 | 0 |
| 71 | Erythema | 0 | 0 | 0 | 0 | 0 |
| | Oedema | 0 | 0 | 0 | 0 | 0 |
| 78 | Erythema | 0 | 0 | 0 | 0 | 0 |
| | Oedema | 0 | 0 | 0 | 0 | 0 |
| 85 | Erythema | 0 | 0 | 0 | 0 | 0 |
| | Oedema | 0 | 0 | 0 | 0 | 0 |

Note:
refer to Table 3 for scoring scales.

TABLE 10B

Individual skin irritation scores of Group 3
treated with Restylane ™ gel

| | | Animal number | | | | |
|---|---|---|---|---|---|---|
| Day | Skin reaction | L076 | L077 | L078 | L079 | L080 |
| 8 | Erythema | 0 | 0 | 0 | 0 | 0 |
| | Oedema | 0 | 0 | 0 | 0 | 0 |
| 15 | Erythema | 0 | 0 | 0 | 0 | 0 |
| | Oedema | 0 | 0 | 0 | 0 | 0 |
| 22 | Erythema | 0 | 0 | 0 | 0 | 0 |
| | Oedema | 0 | 0 | 0 | 0 | 0 |
| 29 | Erythema | 0 | 0 | 0 | 0 | 0 |
| | Oedema | 0 | 0 | 0 | 0 | 0 |
| 36 | Erythema | 0 | 0 | 0 | 0 | 0 |
| | Oedema | 0 | 0 | 0 | 0 | 0 |
| 43 | Erythema | 0 | 0 | 0 | 0 | 0 |
| | Oedema | 0 | 0 | 0 | 0 | 0 |
| 50 | Erythema | 0 | 0 | 0 | 0 | 0 |
| | Oedema | 0 | 0 | 0 | 0 | 0 |
| 57 | Erythema | 0 | 0 | 0 | 0 | 0 |
| | Oedema | 0 | 0 | 0 | 0 | 0 |
| 64 | Erythema | 0 | 0 | 0 | 0 | 0 |
| | Oedema | 0 | 0 | 0 | 0 | 0 |
| 71 | Erythema | 0 | 0 | 0 | 0 | 0 |
| | Oedema | 0 | 0 | 0 | 0 | 0 |
| 78 | Erythema | 0 | 0 | 0 | 0 | 0 |
| | Oedema | 0 | 0 | 0 | 0 | 0 |
| 85 | Erythema | 0 | 0 | 0 | 0 | 0 |
| | Oedema | 0 | 0 | 0 | 0 | 0 |

Note:
refer to Table 3 for scoring scales.

TABLE 11

Mean skin irritation scores of all groups for
HA/GM and Restylane ™ gel

| | Mean irritation scores (n = 5) | | | | | |
|---|---|---|---|---|---|---|
| | HA/GM gel | | | Restylane ™ gel | | |
| Day | Group 1 | Group 2 | Group 3 | Group 1 | Group 2 | Group 3 |
| | Erythema | | | | | |
| 8 | 0 | 0 | 0 | 0 | 0 | 0 |
| 15 | 0 | 0 | 0 | 0 | 0 | 0 |
| 22 | 0 | 0 | 0 | 0 | 0 | 0 |
| 29 | 0 | 0 | 0 | 0 | 0 | 0 |
| 36 | — | 0 | 0 | — | 0 | 0 |
| 43 | — | 0 | 0 | — | 0 | 0 |
| 50 | — | 0 | 0 | — | 0 | 0 |
| 57 | — | 0 | 0 | — | 0 | 0 |
| 64 | — | — | 0 | — | — | 0 |
| 71 | — | — | 0 | — | — | 0 |
| 78 | — | — | 0 | — | — | 0 |
| 85 | — | — | 0 | — | — | 0 |
| mean ± SD | 0 | 0 | 0 | 0 | 0 | 0 |
| | Oedema | | | | | |
| 8 | 0 | 0 | 0 | 0 | 0 | 0 |
| 15 | 0 | 0 | 0 | 0 | 0 | 0 |
| 22 | 0 | 0 | 0 | 0 | 0 | 0 |
| 29 | 0 | 0 | 0 | 0 | 0 | 0 |
| 36 | — | 0 | 0 | — | 0 | 0 |
| 43 | — | 0 | 0 | — | 0 | 0 |
| 50 | — | 0 | 0 | — | 0 | 0 |
| 57 | — | 0 | 0 | — | 0 | 0 |
| 64 | — | — | 0 | — | — | 0 |
| 71 | — | — | 0 | — | — | 0 |
| 78 | — | — | 0 | — | — | 0 |
| 85 | — | — | 0 | — | — | 0 |
| Mean ± SD | 0 | 0 | 0 | 0 | 0 | 0 |

Note:
Refer to Table 3 for scoring scales.

Individual intradermal distension scores are presented in Table 12.

TABLE 12

Individual intradermal distension scores of Group 3 rabbits on Day 85

| Animal | Intradermal distension scores | |
|---|---|---|
| number | HA/GM gel | Restylane ™ gel |
| L076 | 3 | 2 |
| L077 | 3 | 1 |
| L078 | 2 | 3 |
| L079 | 1 | 1 |
| L080 | 1 | 2 |
| | Score 3: 2/5 | Score 3: 1/5 |
| | Score 2: 1/5 | Score 2: 2/5 |
| | Score 1: 2/5 | Score 1: 2/5 |
| Mean | 2.0 | 1.8 |

Note:
Refer to Table 5A for scoring scales

The intradermal distension was assessed on Days 29, 57 and 85 for all groups. The scoring for the intradermal distension was according to Table 5A.

Group 1 (Day 29)

The mean scores for the HA/GM gel on each observation day for erythema and oedema were 0 and 0, respectively. The mean scores for Restylane™ gel on each observation day for erythema and oedema were 0 and 0, respectively. Individual scores for intradermal distension were not measured at Day 29 as there was no observable difference between HA/GM and Restylane™ gel injections sites.

Group 2 (Day 57)

The mean scores for the HA/GM gel on each observation day for erythema and oedema were 0 and 0, respectively. The mean scores for Restylane™ gel on each observation day for erythema and oedema were 0 and 0, respectively.

Individual scores for intradermal distension were not measured at Day 57 as there was no observable difference between HA/GM and Restylane™ gel injection sites.

Group 3 (Day 85)

The mean scores for the HA/GM gel on each observation day for erythema and oedema were 0 and 0, respectively. The mean scores for the Restylane™ gel on each observation day for erythema and oedema were 0 and 0, respectively. The individual score for the intradermal distension at Day 85 for the treatment with the HA/GM gel was 3 for 2/5 animals, 2 for 1/5 animals and 1 for 2/5 animals, with a mean score of 2.0. The individual score for the intradermal distension at Day 85 for the treatment with Restylane™ gel was 3 for 1/5 animals, 2 for 2/5 animals and 1 for 2/5 animals, with a mean score of 1.8.

Histopathology

Individual animal data of histopathological examinations are presented in Table 13. The scoring for the severity of the histologic legions was according to Table 5B.

TABLE 13

Individual histopathology observation

| | | Lesion score | | | |
|---|---|---|---|---|---|
| | | HA/GM gel | | Restylane ™ gel | |
| Group | Animal number | Deep dermal inflammation (score/nature) | New collagen/ fibroblasts within/around the gel | Deep dermal inflammation (score/nature) | New collagen/ fibroblasts within/around the gel |
| 1 | L066 | 2 b | 2 | 1 a | 1 |
| Day 29 | L067 | 3 c | 3 | 1 a | 2 |
| | L068 | 3 b | 2 | 1 a | 1 |
| | L069 | 3 c | 3 | 1 b | 2 |
| | L070 | 3 a | 3 | 1 a | 2 |
| Mean ± SD | | 2.8 ± 0.45 | 2.6 ± 0.55 | 1.0 ± 0.00 | 1.6 ± 0.55 |
| 2 | L071 | 3 b | 3 | 1 a | 2 |
| Day 57 | L072 | 2 b | 3 | 1 a | 2 |
| | L073 | 2 b | 3 | 1 a | 1 |
| | L074 | 3 c | 3 | 1 a | 2 |
| | L075 | 3 c | 3 | 2 a | 2 |
| Mean ± SD | | 2.6 ± 0.55 | 3.0 ± 0.00 | 1.2 ± 0.45 | 1.8 ± 0.45 |
| 3 | L076 | 2 a | 3 | 1 a | 2 |
| Day 85 | L077 | 2 c | 3 | 1 a | 2 |
| | L078 | 1 a | 3 | 2 c | 3 |
| | L079 | 2 c | 2 | 2 d | 3 |
| | L080 | 1 a | 3 | 3 c | 3 |
| Mean ± SD | | 1.6 ± 0.55 | 2.8 ± 0.45 | 1.8 ± 0.84 | 2.6 ± 0.55 |

Notes:
Refer to Table 5B for scoring scales;
Nature: a, lymphohistiocytic; b, histiocytic; c, granulomatous; d, mixed including granulocytes
Scores: 0, normal; 1, minimal change; 2, mild change; 3, moderate change; 4, severe change All sections contained hyaluronic acid gel. Most sections exhibited some degree of dispersal of the gel, with a large cavity containing the gel surrounded by numerous small cavities. All sections exhibited a deep dermal inflammatory reaction accompanied by at least minimal proliferation of fibroblasts and collagen deposition within and/or around the gel.

Deep Dermal Inflammation

Group 9 (Day 29)

Deep dermal inflammation was moderate in 4/5 ears and mild in 1/5 ears treated with HA/GM gel whereas it was minimal in all the 5 ears treated with Restylane™ gel. The nature of the inflammation was histiocytic in 2/5 ears and lymphohistiocytic in 1/5 ears and granulomatous in 2/5 ears treated with HA/GM gel whereas it was histiocytic in 1/5 ears and lymphohistiocytic in 4/5 ears treated with Restylane™ gel. The mean scores for the deep dermal inflammation for HA/GM gel and Restylane™ gel were 2.8 and 1.0, respectively.

Group 2 (Day 57)

Deep dermal inflammation was moderate in 3/5 ears and mild in 2/5 ears treated with HA/GM gel whereas it was minimal in 4/5 ears and mild in 1/5 ears treated with Restylane™ gel. The nature of the inflammation was histiocytic in 3/5 ears and granulomatous in 2/5 ears treated with HA/GM gel whereas it was lymphohistiocytic in all 5 ears treated with Restylane™ gel. The mean scores for the deep dermal inflammation for HA/GM gel and Restylane™ gel were 2.6 and 1.2, respectively.

Group 3 (Day 85)

Deep dermal inflammation was mild in 3/5 ears and minimal in 2/5 ears treated with HA/GM gel whereas it was moderate in 1/5 ears, mild in 2/5 ears and minimal in 2/5 ears treated with Restylane™ gel. The nature of the inflammation was lymphohistiocytic in 3/5 ears and granulomatous in 2/5 ears treated with HA/GM gel whereas it was lymphohistiocytic in 2/5 ears, granulomatous in 2/5 ears and mixed including granulocytes in 1/5 ears treated with Restylane™ gel. The mean scores for the deep dermal inflammation for HA/GM gel and Restylane™ gel were 1.6 and 1.8, respectively.

Comparison Between HA/GM Gel and Restylane™ Gel

The mean lesion scores for inflammation around the HA/GM gel decreased between Day 29 and Day 85 whereas those for Restylane™ were relatively constant from Day 29 to Day 56 and increased from Day 57 to Day 85.

New Collagen/Fibroblasts within and Around the Gel

Group 1 (Day 29)

Figure 11:
FIG. 11. Histological sections of rabbit ear at Day 29. HA/GM gel (B) resulted in increased fibroblasts and new collagen production compared to Restylane™ gel (A).
Figure 11:
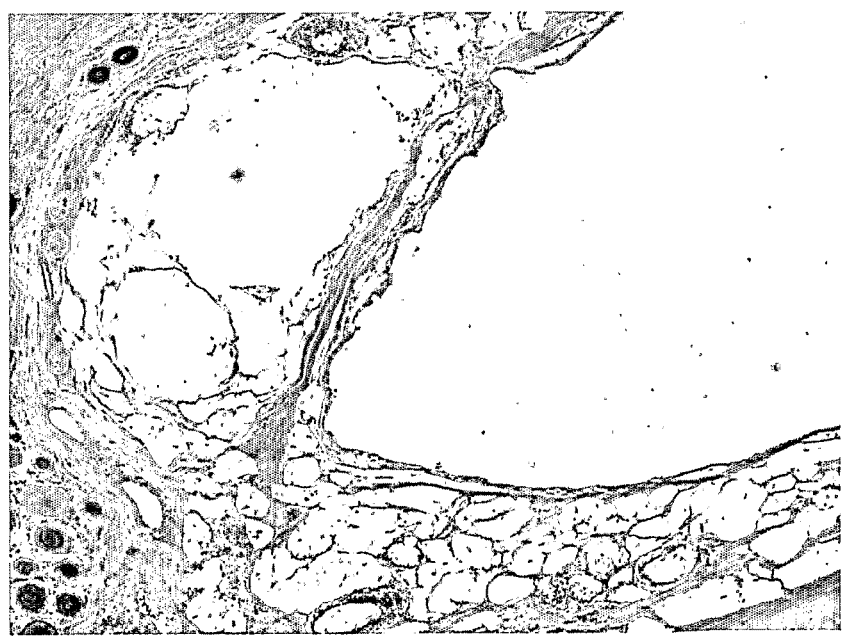

New colle/fibroblasts proliferation within and around the gel was moderate in 3/5 ears and mild in 2/5 ears treated with HA/GM gel whereas it was mild in 3/5 ears and minimal in 2/5 ears treated with Restylane™ gel. The mean scores for the new collagen/fibroblasts proliferation for HA/GM gel and Restylane™ gel were 2.6 and 1.6, respectively. (FIG. 11).

Group 2 (Day 57)

Figure 12:
FIG. 12. Histological sections of rabbit ear at Day 57. HA/GM gel (B) resulted in increased fibroblasts and new collagen production compared to Restylane™ gel (A).
Figure 12:

New collage/fibroblasts proliferation within and around the gel was moderate in all 5 of the ears treated with HA/GM gel whereas it was mild in 4/5 ears and minimal in 1/5 ears treated with Restylane™ gel. The mean scores for the new collagen/fibroblasts proliferation for HA/GM gel and Restylane™ gel were 3.0 and 1.8, respectively. (FIG. 12).

Group 3 (Day 85)

Figure 13:
FIG. 13. Histological sections of rabbit ear at Day 85. (A) Restylane™ gel. (B) HA/GM gel.
Figure 13:
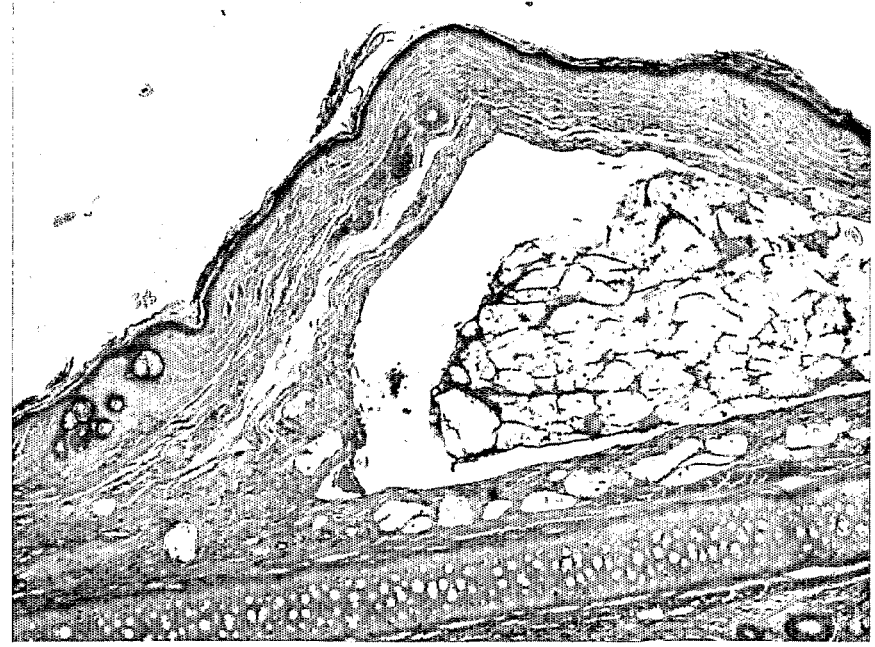

New collage/fibroblasts proliferation within and around the gel was moderate in 4/5 ears and mild in 1/5 ears treated with HA/GM gel whereas it was mild in 3/5 ears and minimal in 2/5 ears treated with Restylane™ gel. The mean scores for the new collagen/fibroblasts proliferation for HA/GM gel and Restylane™ gel were 2.8 and 2.6, respectively. (FIG. 13).

Comparison Between HA/GM Gel and Restylane™ Gel

The mean lesion scores for collagen deposition/fibroblast proliferation around the HA/GM gel remained relatively constant between Day 29, 57 and Day 85 whereas that for Restylane™ gel remained relatively constant from Day 29 to Day 57 and increased from Day 57 to Day 85 (which may reflect individual animal variation).

Dimensions of Injection Site

Individual data on the measurements of the injection site gel are presented in Table 14.

The horizontal dimension for the injection site of the HA/GM gel and the Restylane™ gel ranged from 7 to 12 mm and 6 to 12 mm, respectively. The mean of the horizontal dimension for HA/GM gel and Restylane™ gel was 10 and 9.4 mm, respectively.

Group 2 (Day 57)

The maximum vertical dimension for the injection site of the HA/GM gel and the Restylane™ gel ranged from 1148 to 1736 µm and 788 to 2176 µm, respectively. The maximum vertical dimension of the HA/GM gel was greater than that of Restylane™ gel in 2/5 animals and the same in 1/5 animals and lesser in 2/5 animals. The mean maximum vertical dimension for HA/GM gel and Restylane™ gel was 1362 and 1316 µm, respectively.

The horizontal dimension for the injection site of the HA/GM gel and the Restylane™ gel ranged from 8 to 11 mm and 6 to 11 mm, respectively. The mean of the horizontal dimension for HA/GM gel and Restylane™ gel was 9.4 and 8.8 mm, respectively.

Group 3 (Day 85)

The maximum vertical dimension for the injection site of the HA/GM gel and the Restylane™ gel ranged from 734 to 2176 µm and 614 to 2043 µm, respectively. The maximum vertical dimension of the HA/GM gel was greater than that of Restylane™ gel in 2/5 animals and lesser in 3/5 animals. The mean maximum vertical dimension for HA/GM gel and Restylane™ gel was slightly greater than that of Restylane™ gel, ie, 1340 µm and 1175 µm, respectively.

TABLE 14

Dimensions of injection site gel in rabbit ear skin.

| | | HA/GM gel | | | Restylane ™ gel | | |
|---|---|---|---|---|---|---|---|
| | | Vertical dimension (µm) | | Horizontal | Vertical dimension (µm) | | Horizontal |
| Group | Animal number | Maximum | Main cavity | dimension (mm) | Maximum | Main cavity | dimension (mm) |
| Group 1 | L066 | 1936 | 1215 | 10 | 1242 | 1025 | 11 |
| (Day 29) | L067 | 1348 | 708 | 10 | 1335 | 1335 | 6 |
| | L068 | 1535 | 921 | 11 | 1522 | 841 | 11 |
| | L069 | 2136 | 1282 | 12 | 1068 | 1041 | 12 |
| | L070 | 2723 | 2456 | 7 | 1055 | 788 | 7 |
| Mean ± SD | | 1936 ± 540 | 1316 ± 678 | 10.0 ± 1.9 | 1244 ± 195 | 1006 ± 215 | 9.4 ± 1.0 |
| Group 2 | L071 | 1736 | 1335 | 8 | 2176 | 1976 | 9 |
| (Day 57) | L072 | 1175 | 467 | 11 | 1415 | 1348 | 11 |
| | L073 | 1375 | 841 | 9 | 1375 | 988 | 6 |
| | L074 | 1148 | 627 | 9 | 788 | 267 | 8 |
| | L075 | 1375 | 788 | 10 | 828 | 721 | 10 |
| Mean ± SD | | 1362 ± 235 | 812 ± 327 | 9.4 ± 1.1 | 1316 ± 564 | 1060 ± 646 | 8.8 ± 1.9 |
| Group 3 | L076 | 2176 | 1549 | 8 | 868 | 788 | 5 |
| (Day 85) | L077 | 1148 | 961 | 6 | 614 | 614 | 6 |
| | L078 | 1549 | 1375 | 5 | 2043 | 1749 | 5 |
| | L079 | 734 | 507 | 3 | 948 | 227 | 7 |
| | L080 | 1095 | 788 | 8 | 1402 | 921 | 10 |
| Mean ± SD | | 1340 ± 549 | 1036 ± 426 | 6 ± 2.1 | 1175 ± 562 | 860 ± 561 | 6.6 ± 2.1 |

Note:
*measurement of dimensions made on H & E stained slide.

Group 1 (Day 29)

The maximum vertical dimension for the injection site of the HA/GM gel and the Restylane™ gel ranged from 1348 to 2723 µm and 1055 to 1522 µm, respectively. The maximum vertical dimension of the HA/GM gel was greater than that of Restylane™ gel in 5/5 animals. The mean maximum vertical dimension for HA/GM gel and Restylane™ gel was 1936 and 1244 µm, respectively.

The horizontal dimension for the injection site of the HA/GM gel and the Restylane™ gel ranged from 3 to 8 mm and 5 to 10 mm, respectively. The mean of the horizontal dimension of the injection site for Restylane™ gel was slightly greater than that of the HA/GM gel, ie, 6.6 mm and 6 mm, respectively.

Comparison Between HA/GM Gel and Restylane™ Gel

Between Day 29 and Day 85 there was a large reduction (vertical 596 µm; horizontal 4.0 mm) in the mean dimensions of the injection site of the HA/GM gel as compared to a small reduction (vertical 69 μm; horizontal 2.8 mm) in the mean dimensions of the injection site of the Restylane™ gel.

Discussion

Within each group, there was individual animal variation regarding the dimensions of the injection site and the inflammatory and fibroblastic reaction within and around the gel. Both types of gel stimulated a minimal to moderate inflammatory reaction in the dermis. Both types of gel stimulated a minimal to moderate fibroblast proliferation and collagen deposition in the dermis.

The mean lesion scores for inflammation and collagen deposition/fibroblast proliferation in the dermis was greater for the HA/GM gel on Day 29 and Day 57 but similar to the Restylane™ gel on Day 85 (FIGS. 11-13). The mean dimensions of the injection site at Day 29 were greater for the HA/GM gel but similar to the Restylane™ gel at Day 57. At Day 85, the mean vertical dimension of the HA/GM gel was slightly greater than that of the Restylane™ gel whereas the mean horizontal dimension of the Restylane™ gel was slightly greater than that of the HA/GM gel. The degree of dispersal of the gel appeared greater in the HA/GM gel sections as compared with the Restylane™ gel sections at Days 29 and 57 but there was no apparent difference between the groups at Day 85.

CONCLUSION

No irritation was observed at any test site for the duration of the study. Intradermal distension was slightly less in the Restylane™ injection sites than the HA/GM injection sites at Day 85.

Based on the findings of this study, at Day 29 the maximum dimensions of HA/GM gel were consistently greater than those of Restylane™ gel. At Day 57 and Day 85, differences between the gels were smaller and inconsistent.

This study showed that, at Day 29 and Day 57, HA/GM gel resulted in increased fibroblasts and new collagen production compared to Restylane™ gel.

Example 4

Preparation of Nanoparticles

Chitosan (Sigma, 75-85% deacetylated; medium MW; 500 mg) was dissolved in 1% w/w acetic acid (100 mL). The sample was adjusted to pH 4.8, the volume adjusted to 200 mL with water, and the solution filtered through a 5 micron nylon mesh (final concentration=2.5 mg/mL). Hyaluronic acid (FocusChem; Cosmetic Grade, 8000-15000 Da) was made up to 5 mg/mL in deionised water. Soluble glucomannan was made up to 20.0 mg/mL in deionised water and filtered through a 0.45 micron filter.

For glucomannan containing nanoparticles, chitosan (2.5 mg/mL; 8 mL), glucomannan (20 mg/mL; 4 mL) and water (4.4 mL) were mixed at 1250 rpm at 20° C. Hyaluronic acid (5 mg/mL; 3.6 mL) was then added drop-wise to the stirred chitosan solution.

For non-glucomannan containing nanoparticles, chitosan (2.5 mg/mL; 8 mL) and water (8.4 mL) were mixed at 1000 rpm at 20° C. Hyaluronic acid (5 mg/mL; 3.6 mL) was then added drop-wise to the stirred chitosan solution.

After hyaluronic acid addition, both nanoparticle formulations were left to stir at 1000 rpm for 60 minutes. The samples were then centrifuged at 23,000 rcf for 8 min at 12° C. The pellets were collected and resuspended in water containing propylene glycol (5% w/w) to a final concentration of 9.6 mg/mL. Scanning electron microscope examination of the glucomannan nanoparticles demonstrated nanoparticles up to 200 nm in size.

Example 5

Glucomannan Nanoparticle Pilot Study

Methods

Subjects: Two volunteers were enlisted; a), a 20+ female (Indian origin), b), a 50+ male (Anglo-Saxon origin).

Treatment: If necessary, subjects shaved one of their inner volar forearms (outer in subject b)). Treatment with GM (−) and GM (+) formulations (supplied by Ultraceuticals Pty Ltd, Australia) began on a day designated as Day 0 and continued daily for 14 days. Before treatment, two adhesive templates were placed at separate points of the designated area and marked with indelible pen, to allow dosing and imaging in identical areas each day for the entire duration of the study. One drop of each formulation was placed with a plastic Pasteur pipette in the centre of the template and rubbed in with a gloved fingertip. The liquid was then allowed to evaporate over approximately 10 min, after which the template was removed. On the next day, templates were placed and their positions remarked before dosing.

Imaging: This was performed on Days 0 (before treatment commenced), 3, 5, 7, 10, 12, 14. Images (Multiphoton microscopy (MPM) and Fluorescence lifetime image microscopy (FLIM)) were recorded at 130 μm below the Stratum Corneum surface with a DermaInspect instrument certified for in vivo applications.

Results

No skin irritation was noted following treatment with either of the GM (−) and GM (+) formulations.

Nanoparticles could not be detected, either in the neat formulations, or in the skin following treatment, as their size was below the limit of detection of the instrument under the conditions of use.

Figure 14:
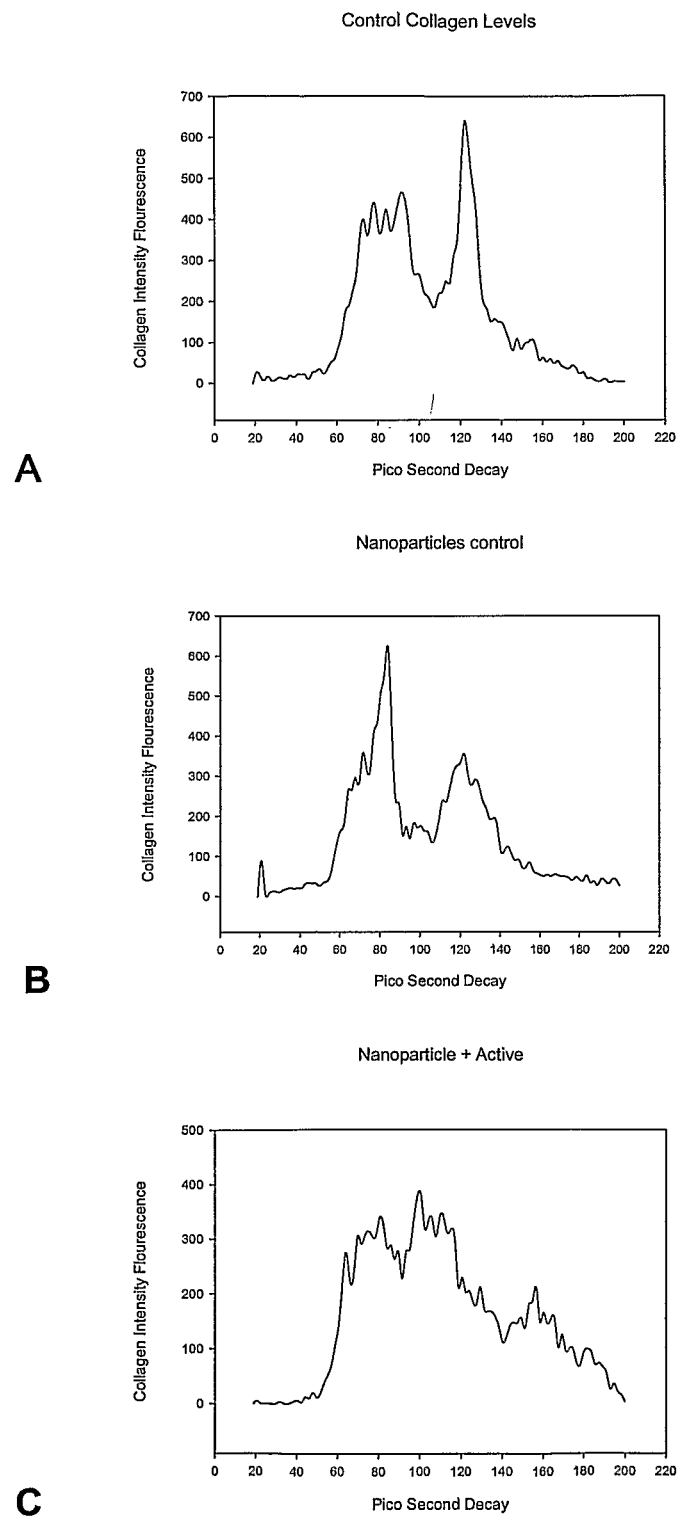
FIG. 14. Plot of histogram quantum yield of, collagen (Y-axis) versus decay time in picoseconds (X-axis). The quantum yield intensity is a measure of photons emitted by collagen and pro-collagen as a result of the NIR excitation the measure is non quantifiable but rather an arbitrary measurement. (A) control untreated; (B) control nanoparticles; (C) nanoparticles plus the active.

The raw data obtained at each imaging session, representing the fluorescence lifetime decay specific for collagen which has a very short decay of 20-200 Pico-second decay histogram, are plotted in FIG. 14. This fast decay is specific to collagen. The left trace (A) corresponds to control untreated; the middle trace (B) is the control nanoparticles; and the right trace (C) is the nanoparticles plus the active. These results show that the two formulations have an effect on collagen production.

Figure 15:
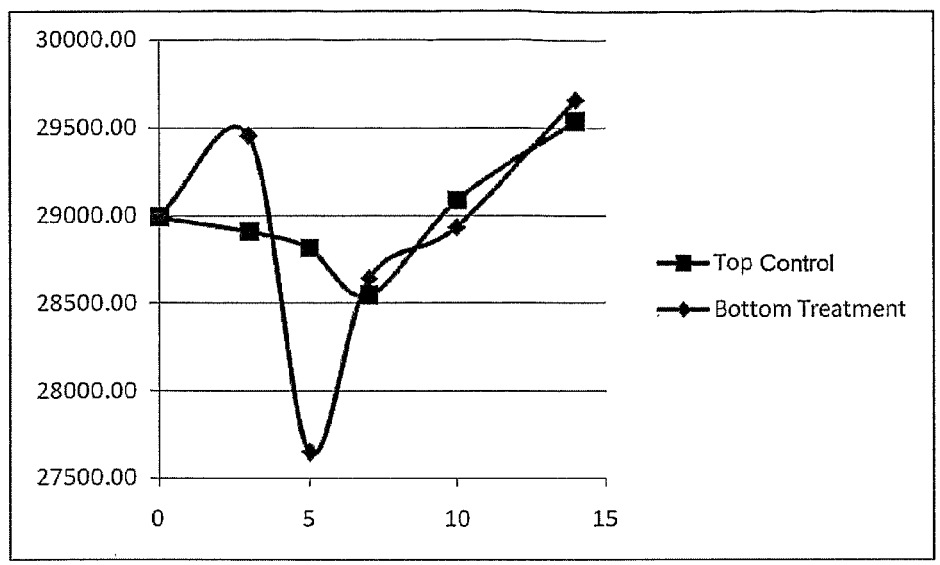
FIG. 15. Quantum Yield map of collagen over 14 days, female aged 20+.
Figure 16:
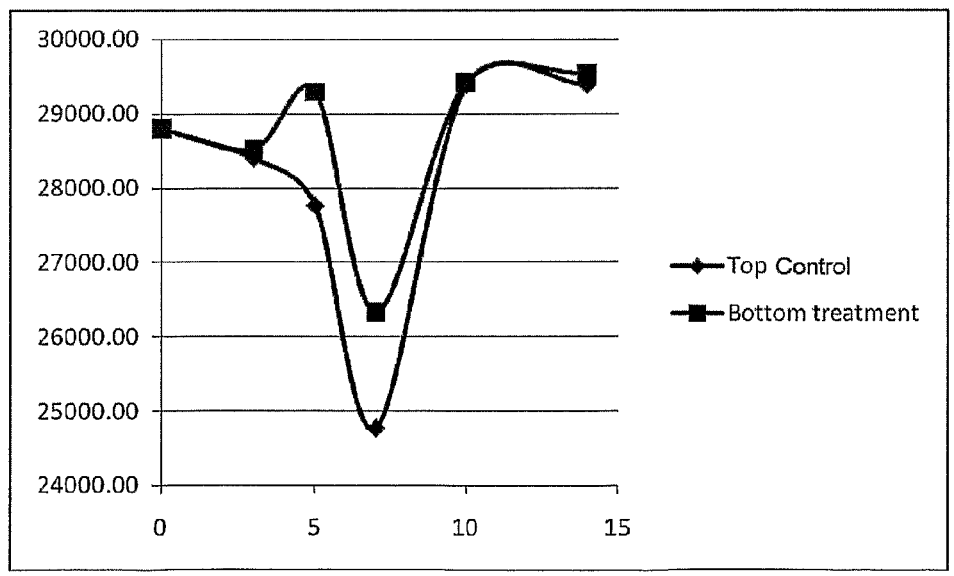
FIG. 16. Quantum Yield map of collagen over 14 days, male aged 50+.

The area under the curve (AUC) was calculated and is shown plotted versus time in days (FIGS. 15 and 16). AUC represents the total quantum yield of collagen, which equates to total collagen present in the sample in vivo.

It is evident from FIGS. 15 and 16 that collagen production peaked at about 3 days for the female subject and 5 days for the male subject, post application after both treatments. With control nanoparticles, collagen production did not peak in the first few days, however a response from matrix metalloproteinase enzyme (MMP) activity was recorded similarly to the nanoparticles plus active. This was followed by an increase in collagen production that continues to increase for the female subject and peaks at day 10 and plateaus for the male subject. The MMP responses are different for both nanoparticles control and nanoparticles plus active.

Discussion

The results can be explained as follows: collagen production and remodelling undergoes a cycle that is finely tuned in normal skin and to a certain extent in damaged skin, eg, due to sun damage or external insult, eg, surgery, burn, etc.

The normal cycle is a balance of collagen production and collagen lysis (driven and moderated by MMPs (in this case collagenase).

Without intending to be bound by a particular theory, it is presently believed that the process of collagen production induction offsets the balance between synthesis and lysis, therefore the balance between the two needs to be maintained. This is seen in the initial peak of collagen production followed by the onset of collagen lysis, which should then be followed by a remodelling stage. It is evident that the treatments of both compounds have achieved the desired response of increasing collagen production. The remodelling aspect of this process was not observed due to the brevity of the trial; however given sufficient time this should be evident, not so much in quantity of collagen produced but rather on the remodelled tissue produced after equilibrium is achieved.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

OECD (2004) Organisation for Economic Co-operation and Development: Test guideline 428. Skin Absorption: in vitro method.

Diembeck, W., Beck, H., Benrch-Kieffer, F., Courtellemont, P., Dupuis, J., Lovell, W., Paye, M., Spengler, J. and Steiling, W. (1999). "Test guidelines for in vitro assessment of dermal absorption and percutaneous penetration of cosmetic ingredients." *Food and Chemical Toxicology* 37: 191-205.

Walters, K. A., Brain, K. R., Dressler, W. E., Green, D. M., Howes, D., James, V. J., Kelling, C. K., Watkinson, A. C. and Getting, S. D. (1997). "Percutaneous penetration of N-Nitroso-N-methyldodecylamine through human skin in vitro: Application from cosmetic vehicles." *Food and Chemical Toxicology* 35: 705-712

Hayes A. and Markovic B. (2002). "Toxicity of Australian essential oil Backhousia citriodora (Lemon myrtle). Part 2. Absorption and Histopathology following application to human skin." *Food and Chemical Toxicology* 41, 1409-1416.

Markovic et al. (1994). "Quantitation of Fc gamma RII mRNA in platelets and megakaryoblastic cell lines by a new method of in situ hybridization."*Journal of Immunological Methods*. 172(1), 105-14.

Markovic, B., Wu, Z. H., Chesterman, C. N. and Chong, B. H. (1995). Quantitation of soluble and membrane bound FcγRIIA (CD32A) mRNA in platelets and megakaryoblastic cell line (MEG-01). *British Journal of Haematology.* 91: 37-42.

Draize J H, Woodward G and Calvery H D (1944) Methods for the study of irritation and toxicity of substances applied topically to the skin and mucous membranes. *Journal of Pharmacology and Experimental Therapy*, 83, 377-390.

The invention claimed is:

1. A method for treating a condition of skin of a mammalian subject in need of such treatment by promoting an accumulation of fibroblasts in the skin and increasing production of collagen in skin, the method comprising delivering to the skin of the subject an active component comprising:

a glucomannan polysaccharide cross linked with hyaluronic acid, or an oligosaccharide derived from glucomannan cross linked with hyaluronic acid, or mixtures or combinations thereof;

wherein the glucomannan polysaccharide or the oligosaccharide derived from glucomannan is derived from konjac root (Amorphophallus konjac);

wherein the glucomannan polysaccharide or the oligosaccharide derived from glucomannan is cross-linked with the hyaluronic acid by ether bonds using a bifunctional epoxide or a polyfunctional epoxide cross-linking agent;

wherein the active component is formulated as a gel, or with an encapsulation vehicle, liposome, or particulate or microfine vehicle, and wherein the treating is selected from the group consisting of regenerating, healing, augmenting, reducing scarring, reducing signs of ageing, heals wounds or ulcers, regenerating atrophic skin due to trauma, skin disease or skin ageing, smoothing wrinkles, increasing skin firmness, and increasing elasticity in ageing skin.

2. The method according to claim 1, wherein the active component is a glucomannan polysaccharide cross linked with hyaluronic acid.

3. The method according to claim 1, wherein the active component comprises glucomannan polysaccharide cross linked with hyaluronic acid, oligosaccharide derived from glucomannan cross linked with the hyaluronic acid, mixtures or combinations thereof, and the hyaluronic acid is in a ratio of 90:10 by weight to 10:90 by weight.

4. The method according to claim 3, wherein the active component comprises glucomannan polysaccharide cross linked with hyaluronic acid or an oligosaccharide derived from glucomannan cross linked with hyaluronic acid, wherein the hyaluronic acid is in a ratio of 20:80 by weight.

5. The method according to claim 1, wherein the active component is injected directly into the skin or subcutaneous tissue of the subject.

6. The method according to claim 1, wherein the active component is applied topically to the skin of the subject.

7. The method according to claim 1, wherein the active component is delivered to the skin of the subject at a concentration of from 0.001 to 100% by weight.

8. The method of claim 3, wherein the ratio of glucomannan polysaccharide or oligosaccharide derived from glucomannan and hyaluronic acid is 15:85 by weight.

9. The method of claim 3, wherein the ratio of glucomannan polysaccharide or oligosaccharide derived from glucomannan and hyaluronic acid is 10:90 by weight.

10. The method of claim 1, wherein the active component is delivered to the skin of the subject at a concentration of from 0.01 to 70% by weight.

11. The method of claim 1, wherein the active component is delivered to the skin of the subject at a concentration of from 1 to 20% by weight.

12. The method of claim 1, wherein the active component comprises glucomannan polysaccharide cross linked with hyaluronic acid.

13. The method according to claim 12, wherein the hyaluronic acid is in a ratio of 90:10 by weight to 10:90 by weight.

14. The method according to claim 13, wherein the hyaluronic acid is in a ratio of 85:15 by weight.

15. The method according to claim 14, wherein the active component is injected directly into the skin or subcutaneous tissue of the subject.

16. The method according to claim 14, wherein the active component is applied topically to the skin of the subject.

17. The method according to claim 14, wherein the active component is delivered to the skin of the subject at a concentration of from 0.001 to 100% by weight.

18. The method according to claim 1 wherein the cross-linking agent is 1,4 butanediol diglycidyl ether.

* * * * *